US012459949B2

(12) United States Patent
Jung et al.

(10) Patent No.: US 12,459,949 B2
(45) Date of Patent: Nov. 4, 2025

(54) LIGHT-EMITTING DEVICE AND METHOD OF MANUFACTURING THE SAME

(71) Applicant: Samsung Display Co., Ltd., Yongin-si (KR)

(72) Inventors: Yunku Jung, Yongin-si (KR); Changhee Lee, Yongin-si (KR); Hyekyoung Choi, Yongin-si (KR); Jaekook Ha, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 647 days.

(21) Appl. No.: 17/660,722

(22) Filed: Apr. 26, 2022

(65) Prior Publication Data

US 2022/0367830 A1 Nov. 17, 2022

(30) Foreign Application Priority Data

May 3, 2021 (KR) ........................ 10-2021-0057477

(51) Int. Cl.
*C07D 487/04* (2006.01)
*C07C 15/28* (2006.01)
(Continued)

(52) U.S. Cl.
CPC ............ *C07D 487/04* (2013.01); *C07C 15/28* (2013.01); *C07C 211/54* (2013.01);
(Continued)

(58) Field of Classification Search
CPC ...... H10K 50/15; H10K 50/125; H10K 50/16; H10K 71/00; H10K 71/421; H10K 85/30;
(Continued)

(56) References Cited

U.S. PATENT DOCUMENTS

| | | | | |
|---|---|---|---|---|
| 11,056,650 B2 | 7/2021 | Kang et al. | | |
| 2015/0218444 A1* | 8/2015 | Kang | H01L 33/56 | 252/519.34 |

(Continued)

FOREIGN PATENT DOCUMENTS

| | | |
|---|---|---|
| CN | 108389982 B | 8/2018 |
| CN | 111781803 A | 10/2020 |

(Continued)

OTHER PUBLICATIONS

Yang et al., "High-resolution patterning of colloidal quantum dots via non-destructive, light-driven ligand crosslinking," Nature Communications, 2020, pp. 1-9, vol. 11, No. 2874.

(Continued)

*Primary Examiner* — Ali Naraghi
*Assistant Examiner* — Christina A Sylvia
(74) *Attorney, Agent, or Firm* — Womble Bond Dickinson (US) LLP

(57) ABSTRACT

Disclosed are a light-emitting device and a method of manufacturing the same. The light-emitting device includes: a first electrode; a second electrode facing the first electrode; an emission layer between the first electrode and the second electrode and including a quantum dot including a first ligand bonded to a surface thereof; and a charge transport layer including an inorganic nanoparticle including a second ligand bonded to a surface thereof, wherein an interface between the emission layer and the charge transport layer includes a cross-link in which the first ligand on the surface of the quantum dot and the second ligand on the surface of the inorganic nanoparticle are linked by a cross-linking agent.

20 Claims, 7 Drawing Sheets

(51) Int. Cl.

| | |
|---|---|
| ***C07C 211/54*** | (2006.01) |
| ***C07C 211/55*** | (2006.01) |
| ***C07C 211/61*** | (2006.01) |
| ***C07C 245/06*** | (2006.01) |
| ***C07C 245/12*** | (2006.01) |
| ***C07C 255/31*** | (2006.01) |
| ***C07C 255/34*** | (2006.01) |
| ***C07C 321/06*** | (2006.01) |
| ***C07D 209/86*** | (2006.01) |
| ***C07D 213/06*** | (2006.01) |
| ***C07D 235/18*** | (2006.01) |
| ***C07D 239/26*** | (2006.01) |
| ***C07D 249/08*** | (2006.01) |
| ***C07D 251/24*** | (2006.01) |
| ***C07D 307/91*** | (2006.01) |
| ***C07D 401/04*** | (2006.01) |
| ***C07D 401/12*** | (2006.01) |
| ***C07D 403/10*** | (2006.01) |
| ***C07D 403/14*** | (2006.01) |
| ***C07D 405/12*** | (2006.01) |
| ***C07D 409/12*** | (2006.01) |
| ***C07D 519/00*** | (2006.01) |
| ***C07F 1/02*** | (2006.01) |
| ***C07F 5/06*** | (2006.01) |
| ***C07F 15/00*** | (2006.01) |
| ***C07F 19/00*** | (2006.01) |
| ***H10K 50/125*** | (2023.01) |
| ***H10K 50/15*** | (2023.01) |
| ***H10K 50/16*** | (2023.01) |
| ***H10K 71/40*** | (2023.01) |
| ***H10K 85/30*** | (2023.01) |
| ***H10K 85/60*** | (2023.01) |
| *B82Y 20/00* | (2011.01) |
| *H10K 102/00* | (2023.01) |
| *H10K 102/10* | (2023.01) |

(52) U.S. Cl.

CPC .......... *C07C 211/55* (2013.01); *C07C 211/61* (2013.01); *C07C 245/06* (2013.01); *C07C 245/12* (2013.01); *C07C 255/31* (2013.01); *C07C 255/34* (2013.01); *C07C 321/06* (2013.01); *C07D 209/86* (2013.01); *C07D 213/06* (2013.01); *C07D 235/18* (2013.01); *C07D 239/26* (2013.01); *C07D 249/08* (2013.01); *C07D 251/24* (2013.01); *C07D 307/91* (2013.01); *C07D 401/04* (2013.01); *C07D 401/12* (2013.01); *C07D 403/10* (2013.01); *C07D 403/14* (2013.01); *C07D 405/12* (2013.01); *C07D 409/12* (2013.01); *C07D 519/00* (2013.01); *C07F 1/02* (2013.01); *C07F 5/06* (2013.01); *C07F 15/0093* (2013.01); *C07F 19/005* (2013.01); *H10K 50/125* (2023.02); *H10K 50/15* (2023.02); *H10K 50/16* (2023.02); *H10K 71/421* (2023.02); *H10K 85/30* (2023.02); *H10K 85/324* (2023.02); *H10K 85/621* (2023.02); *H10K 85/633* (2023.02); *H10K 85/636* (2023.02); *H10K 85/652* (2023.02); *H10K 85/654* (2023.02); *H10K 85/657* (2023.02); *H10K 85/6572* (2023.02); *H10K 85/6574* (2023.02); *B82Y 20/00* (2013.01); *H10K 71/441* (2023.02); *H10K 2102/102* (2023.02); *H10K 2102/103* (2023.02); *H10K 2102/331* (2023.02)

(58) Field of Classification Search

CPC .. H10K 85/324; H10K 85/621; H10K 85/633; H10K 85/636; H10K 85/652; H10K 85/654; H10K 85/657; H10K 85/6572; H10K 85/6574; H10K 2102/102; H10K 2102/103; H10K 2102/331; H10K 50/115; H10K 71/441; H10K 50/13; H10K 85/113; H10K 85/346; H10K 85/60; C07C 15/28; C07C 211/54; C07C 211/55; C07C 211/61; C07C 245/06; C07C 245/12; C07C 255/31; C07C 255/34; C07C 321/06; C07D 209/86; C07D 213/06; C07D 235/18; C07D 239/26; C07D 249/08; C07D 251/24; C07D 307/91; C07D 401/04; C07D 401/12; C07D 403/10; C07D 403/14; C07D 405/12; C07D 409/12; C07D 487/04; C07D 519/00; C07F 1/02; C07F 5/06; C07F 15/0093; C07F 19/005; C07F 3/003; C07F 7/1804; B82Y 20/00; C09K 11/02; C09K 11/08

See application file for complete search history.

(56) References Cited

U.S. PATENT DOCUMENTS

| | | | | |
|---|---|---|---|---|
| 2017/0244033 | A1* | 8/2017 | Lederer .................... | C09D 5/24 |
| 2019/0048259 | A1* | 2/2019 | Kim ........................ | H10K 50/15 |
| 2019/0305240 | A1* | 10/2019 | Angioni ................. | H10K 50/15 |
| 2019/0312204 | A1 | 10/2019 | Kang et al. | |
| 2020/0067005 | A1 | 2/2020 | Park et al. | |
| 2020/0083450 | A1 | 3/2020 | Han et al. | |
| 2020/0144527 | A1 | 5/2020 | Angioni et al. | |
| 2021/0066544 | A1 | 3/2021 | Won et al. | |
| 2021/0104696 | A1 | 4/2021 | Park et al. | |
| 2021/0371737 | A1 | 12/2021 | Jung et al. | |
| 2022/0098481 | A1 | 3/2022 | Jung et al. | |

FOREIGN PATENT DOCUMENTS

| | | | |
|---|---|---|---|
| KR | 10-2019-0117890 | A | 10/2019 |
| KR | 10-2087299 | B1 | 10/2019 |
| KR | 10-2020-0021726 | A | 3/2020 |
| KR | 10-2020-0028657 | A | 3/2020 |
| KR | 10-2021-0028410 | A | 3/2021 |
| KR | 10-2021-0041373 | A | 4/2021 |
| KR | 10-2021-0149971 | A | 12/2021 |
| KR | 10-2022-0043997 | A | 4/2022 |

OTHER PUBLICATIONS

Ho et al., “Review of recent progress in multilayer solution-processed organic light-emitting diodes,” Journal of Photonics for Energy, 2015, pp. 057611-1 to 057611-17, vol. 5, SPIE.

* cited by examiner

LIGHT-EMITTING DEVICE AND METHOD OF MANUFACTURING THE SAME

CROSS-REFERENCE TO RELATED APPLICATION

This application claims priority to and the benefit of Korean Patent Application No. 10-2021-0057477, filed on May 3, 2021, in the Korean Intellectual Property Office, the disclosure of which is incorporated herein by reference in its entirety.

BACKGROUND

1. Field

One or more embodiments relate to a light-emitting device and a method of manufacturing the same.

2. Description of the Related Art

Light-emitting devices are devices that convert electrical energy into light energy. Examples of such light-emitting devices may include organic light-emitting devices in which a light-emitting material is an organic material, and quantum dot light-emitting devices in which the light-emitting material is a quantum dot.

In a light-emitting device, a first electrode is located on a substrate, and a hole transport region, an emission layer, an electron transport region, and a second electrode are sequentially arranged on the first electrode. Holes provided from the first electrode move toward the emission layer through the hole transport region, and electrons provided from the second electrode move toward the emission layer through the electron transport region. Carriers, such as holes and electrons, recombine in the emission layer to produce excitons. These excitons transition from an excited state to a ground state to thereby generate light.

SUMMARY

Aspects according to one or more embodiments are directed toward a light-emitting device and a method of manufacturing the same. In more detail, aspects according to one or more embodiments are directed toward a light-emitting device that has improved efficiency and lifespan due to an improved bonding force between an emission layer and a charge transport layer, and the light-emitting device may be implemented in a flexible device.

Additional aspects will be set forth in part in the description, which follows and, in part, will be apparent from the description, or may be learned by practice of the presented embodiments of the disclosure.

According to an embodiment, a light-emitting device includes a first electrode, a second electrode facing the first electrode, an emission layer between the first electrode and the second electrode and including a quantum dot including a first ligand bonded to a surface thereof, and a charge transport layer between the first electrode and the emission layer and including an inorganic nanoparticle including a second ligand bonded to a surface thereof, wherein an interface between the emission layer and the charge transport layer includes a cross-link in which the first ligand on the surface of the quantum dot and the second ligand on the surface of the inorganic nanoparticle are linked by a cross-linking agent.

In an embodiment, the cross-linking agent may include two or more functional groups, and the two or more functional groups may each independently be an azide group, an alkoxy group, a vinyl group, a thiol group, an amine group, an epoxy group, an oxirane group, a carboxyl group, or any combination thereof.

In an embodiment, the cross-linking agent may be a compound including two functional groups at ends of a chain, respectively.

In an embodiment, the cross-linking agent may include two or more functional groups, and the two or more functional groups may each be an azide group.

In an embodiment, the first ligand bonded to the surface of the quantum dot may be oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, or any combination thereof.

In an embodiment, the first electrode may be an anode, the second electrode may be a cathode, and the charge transport layer may be a hole transport layer.

In an embodiment, the inorganic nanoparticle in the hole transport layer may include $WO_2$, $WO_3$, NiO, $MoO_3$, $Cr_2O_3$, $Bi_2O_3$, CuO, $Cu_2O$, CuI, CuSCN, $Nb_2O_5$, $BaSnO_3$, $Zn_2SnO_4$, $SrTiO_3$, $Zn_2TiO_8$, or any combination thereof.

In an embodiment, the second ligand bonded to the surface of the inorganic nanoparticle in the hole transport layer may be oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, alkyl trimethoxy silane, mercaptopropionic acid, tert-butoxyamino acid, carbazole-substituted alkyl carboxylic acid, pyrene-substituted alkyl carboxylic acid, or any combination thereof.

In an embodiment, the first electrode may be a cathode, the second electrode may be an anode, and the charge transport layer may be an electron transport layer.

In an embodiment, the inorganic nanoparticle in the electron transport layer may include ZnO, $TiO_2$, $SnO_2$, $In_2O_3$, $WO_3$, $Nb_2O_3$, $CeO_x$, Al-doped ZnO, Mg-doped ZnO, Li-doped ZnO, Y-doped ZnO, Al-doped $TiO_2$, Mg-doped $TiO_2$, Li-doped $TiO_2$, Y-doped $TiO_2$, or any combination thereof.

In an embodiment, the second ligand bonded to the surface of the inorganic nanoparticle in the electron transport layer may be oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, alkyl trimethoxy silane, mercaptopropionic acid, tert-butoxyamino acid, carbazole-substituted alkyl carboxylic acid, pyrene-substituted alkyl carboxylic acid, or any combination thereof.

In an embodiment, the quantum dot may include a first quantum dot and a second quantum dot, and the emission layer may include a cross-link in which a first ligand on a surface of the first quantum dot and a first ligand on a surface of the second quantum dot are linked by the cross-linking agent.

In an embodiment, the light-emitting device may further include a second charge transport layer between the emission layer and the second electrode and including an inorganic nanoparticle including a third ligand bonded to a surface thereof, wherein an interface between the emission layer and the second charge transport layer may include a cross-link in which the first ligand on the surface of the quantum dot and the third ligand on the surface of the inorganic nanoparticle in the second charge transport layer are linked by the cross-linking agent.

In an embodiment, the first electrode may be an anode, the second electrode may be a cathode, the charge transport layer may be a hole transport layer, and the second charge transport layer may be an electron transport layer.

In an embodiment, the emission layer may include a first emission layer and a second emission layer, a first ligand bonded to a surface of a first quantum dot included in the quantum dot in the first emission layer may be a hole-transporting ligand, and a first ligand bonded to a surface of a second quantum dot included in the quantum dot in the second emission layer may be an electron-transporting ligand.

According to another embodiment, a method of manufacturing the light-emitting device includes:

preparing a first electrode, forming a charge transport layer by providing, on the first electrode, an inorganic nanoparticle composition including an inorganic nanoparticle and a solvent, the inorganic nanoparticle including a second ligand bonded to a surface thereof, forming a preliminary emission layer by providing, on the charge transport layer, a quantum dot composition including a quantum dot, a cross-linking agent, and a solvent, the quantum dot including a first ligand bonded to a surface thereof, forming an emission layer by performing at least one of a heat treatment and a UV irradiation on the preliminary emission layer, and forming a second electrode on the emission layer.

In an embodiment, the forming of the emission layer may further include cross-linking the first ligand and the second ligand by performing the at least one of the heat treatment and the UV irradiation on the preliminary emission layer.

In an embodiment, the forming of the emission layer may further include cross-linking a first ligand on a surface of a first quantum dot included in the quantum dot and a first ligand on a surface of a second quantum dot included in the quantum dot by performing the at least one of the heat treatment and the UV irradiation on the preliminary emission layer.

In an embodiment, the method may further include forming a second charge transport layer by providing a second inorganic nanoparticle composition on the emission layer, and the second inorganic nanoparticle composition may include a solvent and an inorganic nanoparticle including a third ligand bonded to a surface thereof.

In an embodiment, the forming of the second charge transport layer may further include cross-linking the first ligand and the third ligand by performing at least one of a heat treatment and a UV irradiation on the second inorganic nanoparticle composition.

In an embodiment, the quantum dot composition may have a viscosity of about 1 cP to about 10 cP and a surface tension of about 10 dynes/cm to about 40 dynes/cm.

BRIEF DESCRIPTION OF THE DRAWINGS

The above and other aspects, features, and enhancements of certain embodiments of the disclosure will be more apparent from the following description taken in conjunction with the accompanying drawings, in which.

DETAILED DESCRIPTION

Figure 1:
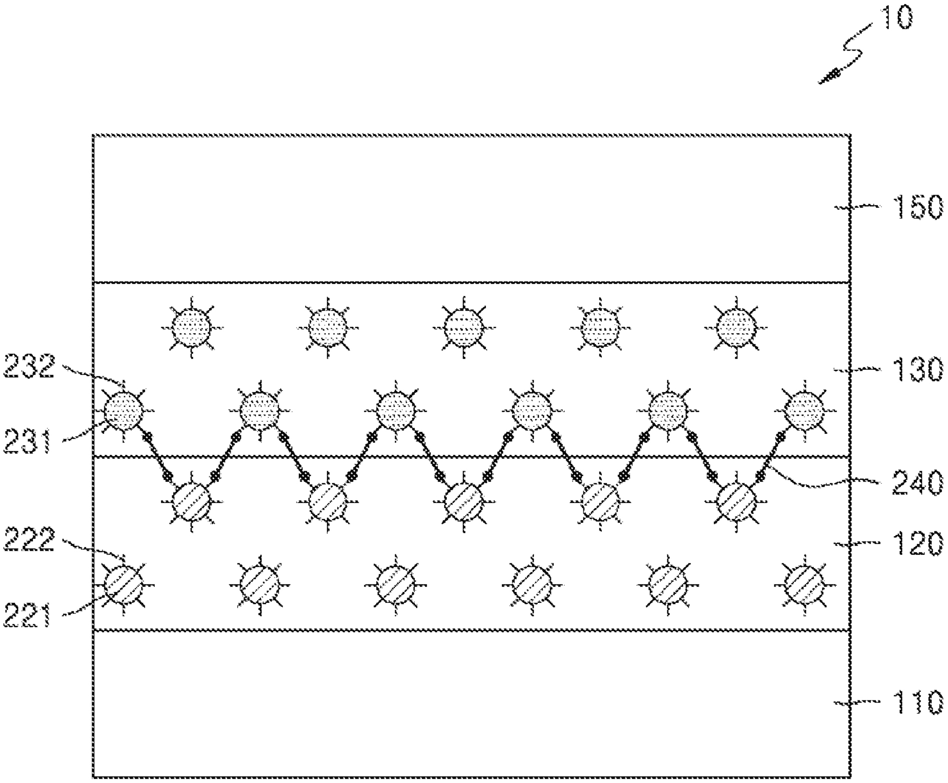
FIG. 1 is a schematic view of a light-emitting device according to an embodiment.

Reference will now be made in more detail to embodiments, examples of which are illustrated in the accompanying drawings, wherein like reference numerals refer to like elements throughout the specification. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, the expression "at least one of a, b and c" indicates only a, only b, only c, both a and b, both a and c, both b and c, all of a, b, and c, or variations thereof.

Because the disclosure may have diverse modified embodiments, embodiments are illustrated in the drawings and are described in the detailed description. An effect and a characteristic of the disclosure, and a method of accomplishing these will be apparent when referring to embodiments described with reference to the drawings. The disclosure may, however, be embodied in many different forms and should not be construed as limited to the embodiments set forth herein.

It will be understood that although the terms "first," "second," etc., as used herein may be used to describe various components, these components should not be limited by these terms. These terms are only used to distinguish one component from another.

An expression used in the singular encompasses the expression of the plural, unless it has a clearly different meaning in the context.

It will be further understood that the terms "includes" and/or "comprises" as used herein specify the presence of stated features or elements, but do not preclude the presence or addition of one or more other features or elements. Unless defined otherwise, the terms "include," or "have" may refer to both the case of consisting of features or components described in the specification and the case of further including other features or components.

The term "Group II" as used herein may include a Group IIA element and a Group IIB element on the IUPAC periodic table, and examples of the Group II element may include Cd, Mg, and Zn, but embodiments are not limited thereto.

The term "Group III" as used herein may include a Group IIIA element and a Group IIIB element on the IUPAC periodic table, and examples of the Group III element may include Al, In, Ga, and Tl, but embodiments are not limited thereto.

The term "Group IV" as used herein may include a Group IVA element and a Group IVB element on the IUPAC periodic table, and examples of the Group IV element may include Si, Ge, and Sn, but embodiments are not limited thereto. The term "metal" as used herein may include a metalloid such as Si.

The term "Group V" as used herein may include a Group VA element on the IUPAC periodic table, and examples of the Group V element may include N, P, As, Sb, and Bi, but embodiments are not limited thereto.

The term "Group VI" as used herein may include a Group VIA element on the IUPAC periodic table, and examples of the Group VI element may include O, S, Se, and Te, but embodiments are not limited thereto.

Hereinafter, a light-emitting device according to an embodiment will be described.

Description of FIG. 1

FIG. 1 is a schematic cross-sectional view of a light-emitting device 10 according to an embodiment. The light-emitting device 10 includes a first electrode 110, a charge transport layer 120, an emission layer 130, and a second electrode 150.

Hereinafter, the structure of the light-emitting device 10 according to an embodiment and a method of manufacturing the light-emitting device 10 will be described in connection with FIG. 1.

First Electrode 110

In FIG. 1, a substrate may be additionally located under the first electrode 110 and/or above the second electrode 150. As the substrate, a glass substrate and/or a plastic substrate may be utilized. In one or more embodiments, the substrate may be a flexible substrate, and may include plastics with suitable (or excellent) heat resistance and durability, such as polyimide, polyethylene terephthalate (PET), polycarbonate, polyethylene naphthalate, polyarylate (PAR), polyetherimide, or any combination thereof.

The first electrode 110 may be formed by, for example, depositing or sputtering a material for forming the first electrode 110 on the substrate. When the first electrode 110 is an anode, a high work function material that facilitates injection of holes may be utilized as a material for forming the first electrode 110.

The first electrode 110 may be a reflective electrode, a semi-transmissive electrode, or a transmissive electrode. When the first electrode 110 is a transmissive electrode, indium tin oxide (ITO), indium zinc oxide (IZO), tin oxide ($SnO_2$), zinc oxide (ZnO), or any combination thereof may be utilized as a material for forming the first electrode 110. In one or more embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combination thereof may be utilized as a material for forming the first electrode 110.

The first electrode 110 may have a single-layered structure consisting of a single layer or a multi-layered structure including a plurality of layers. In an embodiment, the first electrode 110 may have a three-layered structure of ITO/Ag/ITO.

Charge Transport Layer 120 and Emission Layer 130

The emission layer 130 may be located between the first electrode 110 and the second electrode 150, and the emission layer 130 may include a quantum dot (e.g., a plurality of quantum dots) 231 including a first ligand 232 bonded to a surface thereof.

The charge transport layer 120 may be located between the first electrode 110 and the emission layer 130, and the charge transport layer 120 may include an inorganic nanoparticle 221 including a second ligand 222 bonded to a surface thereof.

An interface between the emission layer 130 and the charge transport layer 120 may include a cross-link (e.g., a cross-linked structure) in which the first ligand 232 on the surface of the quantum dot 231 and the second ligand 222 on the surface of the inorganic nanoparticle 221 are linked by a cross-linking agent 240.

The cross-linking agent 240 may include two or more functional groups. In an embodiment, the cross-linking agent 240 may be a compound including two functional groups at ends of a chain, respectively (e.g., the cross-linking agent 240 may be a compound including one or two functional groups at ends of its molecular chain). The cross-linking agent 240 may be chemically reacted with molecules of the first ligand 232 at an end of the chain and molecules of the second ligand 222 at another end of the chain to respectively form a covalent bond, thereby cross-linking the quantum dot 231 and the inorganic nanoparticle 221.

In an embodiment, the functional groups in the cross-linking agent 240 may each independently be an azide group, an alkoxy group, a vinyl group, a thiol group, an amine group, an epoxy group, an oxirane group, a carboxyl group, or any combination thereof.

In an embodiment, each of the functional groups in the cross-linking agent 240 may be an azide group, but embodiments are not limited thereto.

In an embodiment, the cross-linking agent 240 may be a compound including two functional groups selected from an azide group, an alkoxy group, a vinyl group, a thiol group, an amine group, an epoxy group, an oxirane group, and a carboxyl group at ends of a chain, respectively. In an embodiment, the cross-linking agent 240 may be a compound including one or two functional groups selected from an azide group, an alkoxy group, a vinyl group, a thiol group, an amine group, an epoxy group, an oxirane group, and a carboxyl group at ends of a chain, respectively.

In one or more embodiments, the cross-linking agent 240 may include a metal complex. A metal in the metal complex may be Fe, Co, Ni, Zn, Cu, Ru, Rh, Pd, Os, Ir, or Pt. In an embodiment, the metal complex may be a Pt complex or a Zn complex, but embodiments are not limited thereto.

A ligand coordinated with the metal in the metal complex may include $OH^-$, $NH_3^-$, a halogen ion, an aromatic or alicyclic amine, an aromatic or alicyclic ether, an aromatic or alicyclic ester, an aromatic or alicyclic ketone, a $C_1$-$C_{60}$ heterocyclic group, or any combination thereof. In addition, the metal complex may include an azide group, an alkoxy group, a vinyl group, a thiol group, an amine group, an epoxy group, an oxirane group, a carboxyl group, or any combination thereof as a ligand and as the functional group.

In an embodiment, the cross-linking agent 240 may be at least one selected from the following compounds, but embodiments are not limited thereto.

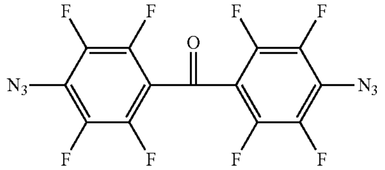

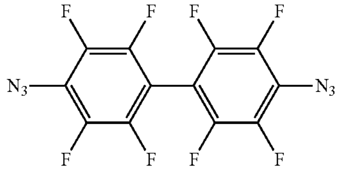

-continued

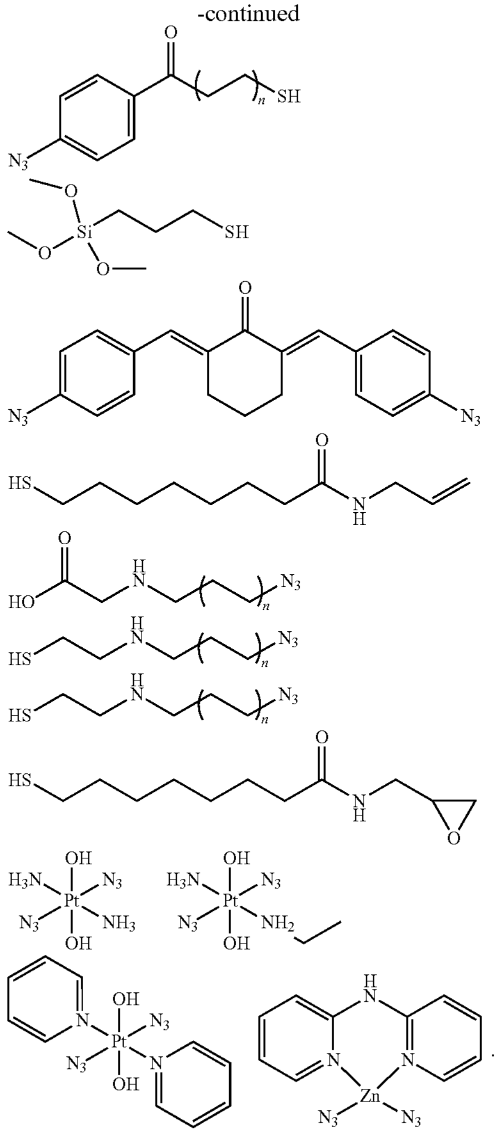

In the above compounds, n may be an integer from 1 to 5.

In related art, an interface between an emission layer and a charge transport layer of a quantum dot light-emitting device is bonded by a weak Van der Waals force, (e.g., a weak Van der Waals force acts at the interface between an emission layer and a charge transport layer of a quantum dot light-emitting device) and thus may be vulnerable to external physical stress. In addition, when the charge transport layer is formed of inorganic nanoparticles, due to void defects (e.g., existence of voids or pores in the charge transport layer and/or the emission layer) that may occur in a stacked structure of quantum dots and inorganic nanoparticles, there may be a leakage current that does not contribute to light emission, and thus, efficiency of the light-emitting device may decrease, and the light-emitting device may deteriorate.

In the light-emitting device 10 according to an embodiment, because the cross-linking agent 240 cross-links the first ligand 232 and the second ligand 222, the bonding force between the charge transport layer 120 and the emission layer 130 may be improved. For example, whereas the Van der Waals force between the charge transport layer 120 and the emission layer 130 is only about 1 kJ/mol, the binding energy when the cross-linking is formed may increase up to about 200 kJ/mol to about 500 kJ/mol. As a result, an interface separation due to external energy and/or physical stress applied to the light-emitting device 10 may be prevented or substantially prevented, and stability of the device may be secured. Accordingly, in the light-emitting device 10, due to prevention or reduction of a leakage current generated at the interface, and prevention or reduction of damage to the charge transport layer 120 resulting therefrom, luminescence efficiency of the device and/or lifespan of the device may be improved. Also, the light-emitting device 10 may be implemented in a flexible device having a flexible form, a rollable form, and/or the like.

In the present specification, a quantum dot 231 refers to a crystal of a semiconductor compound, and may include any suitable material capable of emitting light of various suitable emission wavelengths according to the size of the crystal.

A diameter of the quantum dot 231 may be, for example, in a range of about 1 nm to about 10 nm.

The quantum dot 231 may be synthesized by a wet chemical process, a metal organic chemical vapor deposition process, a molecular beam epitaxy process, or any process similar thereto.

The wet chemical process is a method of growing a quantum dot 231 particle crystal by mixing a precursor material with an organic solvent. When the crystal grows, the organic solvent may naturally serve as a dispersant coordinated on the surface of the quantum dot 231 crystal and control the growth of the crystal. Thus, the wet chemical process may be easier to perform than the vapor deposition process such as a metal organic chemical vapor deposition (MOCVD) or a molecular beam epitaxy (MBE) process. Further, the growth of quantum dot 231 particles may be controlled with a lower manufacturing cost.

The quantum dot 231 may include a Group II-VI semiconductor compound, a Group III-V semiconductor compound, a Group III-VI semiconductor compound, a Group I-III-VI semiconductor compound, a Group IV-VI semiconductor compound, a Group IV element or semiconductor compound, or any combination thereof.

Examples of the Group II-VI semiconductor compound may include: a binary compound, such as CdSe, CdTe, ZnS, ZnSe, ZnTe, ZnO, HgS, HgSe, HgTe, MgSe, and/or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound, such as CdZnSeS, CdZnSeTe, CdZnSTe, CdHgSeS, CdHgSeTe, CdHgSTe, HgZnSeS, HgZnSeTe, and/or HgZnSTe; or any combination thereof.

Examples of the Group III-V semiconductor compound may include: a binary compound, such as GaN, GaP, GaAs, GaSb, AlN, AlP, AlAs, AlSb, InN, InP, InAs, and/or InSb; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, and/or InPSb; a quaternary compound, such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, and/or InAlPSb; or any combination thereof. In some embodiments, the Group III-V semiconductor compound may further include a Group II element. Examples of the Group III-V semiconductor compound further including the Group II element may include InZnP, InGaZnP, InAlZnP, etc.

Examples of the Group III-VI semiconductor compound may include: a binary compound, such as GaS, GaSe, $Ga_2Se_3$, GaTe, InS, InSe, $In_2S_3$, $In_2Se_3$, and/or InTe; a ternary compound, such as $InGaS_3$, and/or $InGaSe_3$; or any combination thereof.

Examples of the Group I-III-VI semiconductor compound may include: a ternary compound, such as AgInS, $AgInS_2$, CuInS, $CuInS_2$, $CuGaO_2$, $AgGaO_2$, and/or $AgAlO_2$; or any combination thereof.

Examples of the Group IV-VI semiconductor compound may include: a binary compound, such as SnS, SnSe, SnTe, PbS, PbSe, and/or PbTe; a ternary compound, such as SnSeS, SnSeTe, SnSTe, PbSeS, PbSeTe, PbSTe, SnPbS, SnPbSe, and/or SnPbTe; a quaternary compound, such as SnPbSSe, SnPbSeTe, and/or SnPbSTe; or any combination thereof.

The Group IV element or semiconductor compound may include: an elementary substance, such as Si and/or Ge; a binary compound, such as SiC and/or SiGe; or any combination thereof.

Each element included in a multi-element compound such as the binary compound, the ternary compound, and/or the quaternary compound, may exist in a particle at a uniform concentration or a non-uniform concentration.

In some embodiments, the quantum dot 231 may have a single structure or a core-shell dual structure. In the case of the quantum dot 231 having a single structure, the concentration of each element included in the corresponding quantum dot may be uniform. In an embodiment, in a core-shell dual structure, the material contained in the core and the material contained in the shell may be different from each other.

The shell of the quantum dot 231 may serve as a protective layer for preventing or substantially preventing chemical denaturation of the core to maintain semiconductor characteristics and/or as a charging layer for imparting electrophoretic characteristics to the quantum dot 231. The shell may be a single layer or a multi-layer. The interface between the core and the shell may have a concentration gradient in which the concentration of an element existing in the shell is decreased as the location is closer to the center of the core.

Examples of the shell of the quantum dot 231 may be an oxide of metal, metalloid, and/or non-metal, a semiconductor compound, and any combination thereof.

Examples of the oxide of metal, metalloid, or non-metal may include: a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound, such as $MgAl_2O_4$, $CoFe_2O_4$, $NiFe_2O_4$, and/or $CoMn_2O_4$; or any combination thereof. Examples of the semiconductor compound may include, as described herein, a Group II-VI semiconductor compound, a Group III-V semiconductor compound, a Group III-VI semiconductor compound, a Group I-III-VI semiconductor compound, a Group IV-VI semiconductor compound, or any combination thereof. In an embodiment, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot 231 may be about 45 nm or less, for example, about 40 nm or less, for example, about 30 nm or less, and within these ranges, color purity or color reproducibility may be increased. In addition, because light emitted through the quantum dot 231 is emitted in all directions, a wide viewing angle may be improved.

In addition, the quantum dot 231 may be, for example, a spherical, pyramidal, multi-arm, or cubic nanoparticle, nanotube, nanowire, nanofiber, and/or nanoplate.

Because an energy band gap may be adjusted by controlling the size of the quantum dot 231, light having various suitable wavelength bands may be obtained in the quantum dot emission layer 130. Therefore, by utilizing quantum dots 231 of different sizes, a light-emitting device that emits light of various suitable wavelengths may be implemented. In some embodiments, the size of the quantum dot 231 may be selected to emit red, green and/or blue light. In addition, the size of the quantum dot 231 may be configured to emit white light by combining light of various suitable colors.

The first ligand 232 is coordinate-bonded to the surface of the quantum dot 231. The first ligand 232 may be: carboxylic acid, such as oleic acid, caproic acid, propionic acid, benzoic acid, cinnamic acid, and/or adamantyl acid; thiol, such as methanethiol, ethanethiol, propanethiol, butanethiol, pentanethiol, hexanethiol, octanethiol, 2-ethylhexane-1-thiol, 1-dodecanethiol, hexadecanethiol, octadecanethiol, benzylthiol, and/or thiophenol; amine, such as methylamine, ethylamine, propylamine, butylamine, pentylamine, hexylamine, octylamine, dodecylamine, hexadecylamine, octadecylamine, dimethylamine, diethylamine, dipropylamine, and/or oleyl amine; and/or phosphine oxide, such as methylphosphine oxide, ethylphosphine oxide, propylphosphine oxide, butylpropylphosphine oxide, and/or trioctylphosphine oxide. In an embodiment, the first ligand 232 bonded to the surface of the quantum dot 231 may be oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, or any combination thereof, but embodiments are not limited thereto.

In an embodiment, the emission layer 130 may include a first emission layer and a second emission layer, a first ligand 232 bonded to a surface of a quantum dot 231 in the first emission layer may be a hole-transporting ligand, and a first ligand 232 bonded to a surface of a quantum dot 231 in the second emission layer may be an electron-transporting ligand.

In an embodiment, the first electrode 110 may be an anode, the second electrode 150 may be a cathode, the first emission layer may be located between the first electrode 110 and the second emission layer, and the hole-transporting ligand may be cross-linked with the second ligand 222 of the charge transport layer 120 via the cross-linking agent 240.

In an embodiment, the electron-transporting ligand may be 1-dodecanethiol, but embodiments are not limited thereto.

The electron-transporting ligand may include an aliphatic hydrocarbon group to facilitate injection of electrons into the emission layer 130.

In an embodiment, the first electrode 110 may be a cathode, the second electrode 150 may be an anode, the second emission layer may be located between the first electrode 110 and the first emission layer, and the electron-transporting ligand may be cross-linked with the second ligand 222 of the charge transport layer 120 via the cross-linking agent 240.

The charge transport layer 120 may have hole-transporting characteristics or electron-transporting characteristics. According to carrier-transporting characteristics of the charge transport layer 120, the inorganic nanoparticle 221 may include a metal oxide having hole-transporting characteristics or electron-transporting characteristics. In an embodiment, the inorganic nanoparticle 221 may include a p-type metal oxide or an n-type metal oxide.

In an embodiment, by utilizing the inorganic nanoparticle 221 instead of an organic material that is vulnerable to moisture and/or oxygen in the charge transport layer 120, deterioration of the light-emitting device 10 due to penetration of moisture and/or oxygen may be minimized or reduced.

The second ligand 222 is coordinate-bonded to the surface of the inorganic nanoparticle 221. The second ligand 222 may be: carboxylic acid, such as oleic acid, caproic acid, propionic acid, benzoic acid, cinnamic acid, adamantyl acid, carbazole-substituted alkyl carboxylic acid, and/or pyrene-substituted alkyl carboxylic acid; thiol, such as methanethiol, ethanethiol, propanethiol, butanethiol, pentanethiol, hexanethiol, octanethiol, 2-ethylhexane-1-thiol, 1-dodecanethiol, hexadecanethiol, octadecanethiol, benzylthiol, and/or thiophenol; amine, such as methylamine, ethylamine, propylamine, butylamine, pentylamine, hexylamine, octylamine, dodecylamine, hexadecylamine, octadecylamine, dimethylamine, diethylamine, dipropylamine, and/or oleyl amine; phosphine oxide, such as methylphosphine oxide, ethylphosphine oxide, propylphosphine oxide, butylpropylphosphine oxide, and/or trioctylphosphine oxide; alkyl trialkoxy silane such as propyl trimethoxy silane; mercaptopropionic acid; and/or tert-butoxyamino acid. In an embodiment, the second ligand 222 bonded to the surface of the inorganic nanoparticle 221 may be oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, alkyl trimethoxy silane, mercaptopropionic acid, tert-butoxyamino acid, carbazole-substituted alkyl carboxylic acid, pyrene-substituted alkyl carboxylic acid, or any combination thereof.

In an embodiment, the first electrode 110 may be an anode, the second electrode 150 may be a cathode, and the charge transport layer 120 may be a hole transport layer.

In an embodiment, an inorganic nanoparticle 221 in the hole transport layer may include a p-type metal oxide. In an embodiment, the inorganic nanoparticle 221 in the hole transport layer may include $WO_2$, $WO_3$, NiO, $MoO_3$, $Cr_2O_3$, $Bi_2O_3$, CuO, $Cu_2O$, CuI, CuSCN, $Nb_2O_5$, $BaSnO_3$, $Zn_2SnO_4$, $SrTiO_3$, $Zn_2TiO_8$, or any combination thereof.

In an embodiment, a second ligand 222 bonded to a surface of the inorganic nanoparticle 221 in the hole transport layer may be oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, alkyl trimethoxy silane, mercaptopropionic acid, tert-butoxyamino acid, carbazole-substituted alkyl carboxylic acid, pyrene-substituted alkyl carboxylic acid, or any combination thereof.

In an embodiment, the light-emitting device 10 may further include a hole injection layer located between the first electrode 110 and the hole transport layer and/or an electron transport region located between the emission layer 130 and the second electrode 150.

In an embodiment, the hole injection layer and the electron transport region may include organic materials and/or inorganic materials. A material for the hole injection layer and a material for the electron transport region may be understood by referring to the description of the hole injection layer and the electron transport region below.

In one or more embodiments, the first electrode 110 may be a cathode, the second electrode 150 may be an anode, and the charge transport layer 120 may be an electron transport layer.

In an embodiment, an inorganic nanoparticle 221 in the electron transport layer may include an n-type metal oxide. In an embodiment, the inorganic nanoparticle 221 in the electron transport layer may include ZnO, $TiO_2$, $SnO_2$, $In_2O_3$, $WO_3$, $Nb_2O_3$, $CeO_x$, Al-doped ZnO, Mg-doped ZnO, Li-doped ZnO, Y-doped ZnO, Al-doped $TiO_2$, Mg-doped $TiO_2$, Li-doped $TiO_2$, Y-doped $TiO_2$, or any combination thereof.

A second ligand 222 bonded to a surface of the inorganic nanoparticle 221 in the electron transport layer may be oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, alkyl trimethoxy silane, mercaptopropionic acid, tert-butoxyamino acid, carbazole-substituted alkyl carboxylic acid, pyrene-substituted alkyl carboxylic acid, or any combination thereof.

In an embodiment, the light-emitting device 10 may further include an electron injection layer located between the first electrode 110 and the electron transport layer and/or a hole transport region located between the emission layer 130 and the second electrode 150.

In an embodiment, the electron injection layer and the hole transport region may include organic materials and/or inorganic materials. A material for the electron injection layer and a material for the hole transport region may be understood by referring to the description of the electron injection layer and the hole transport region below.

Figure 2:
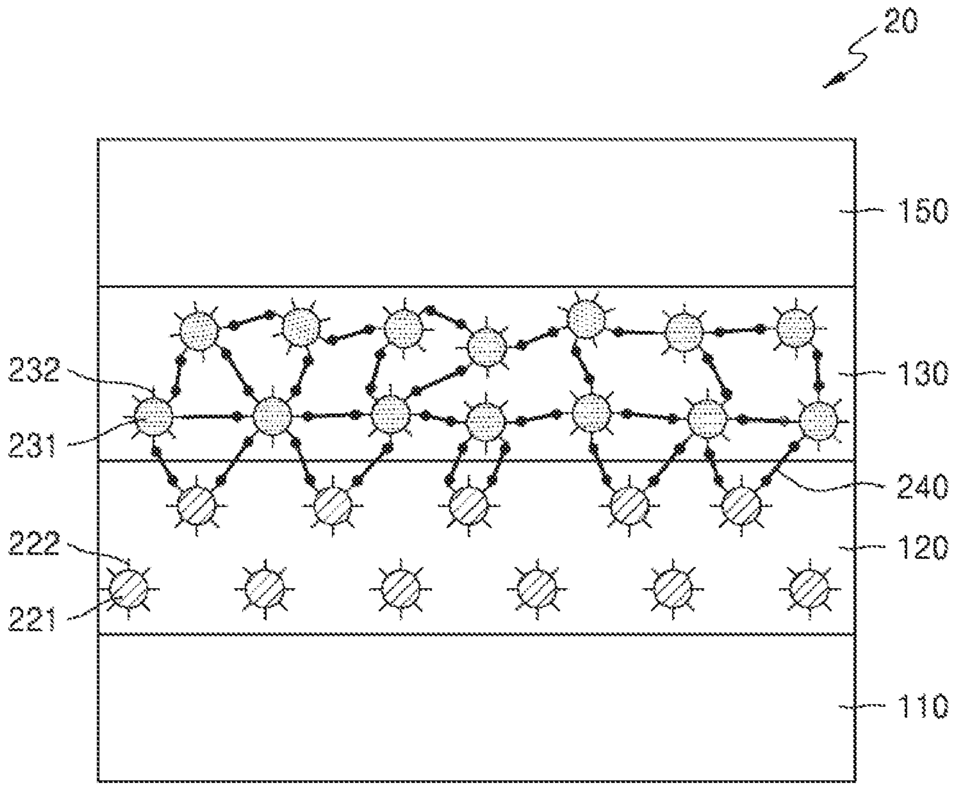
FIG. 2 is a schematic view of a light-emitting device according to another embodiment.

Description of FIG. 2

FIG. 2 is a schematic cross-sectional view of a light-emitting device 20 according to another embodiment. The emission layer 130 of the light-emitting device 20 includes a cross-link (e.g., a cross-linked structure) in which a first ligand 232 on a surface of one quantum dot 231 and a first ligand 232 on a surface of another quantum dot 231 are linked by the cross-linking agent 240.

The cross-link of the quantum dots 231 may be formed, for example, by chemically reacting the first ligands 232 with the cross-linking agent 240 in a thermal curing or UV curing step in a solution process for forming the emission layer 130. Through such a cross-link, physical and chemical stability of the emission layer 130 may be secured.

Because the emission layer 130 further includes the cross-link between the quantum dots 231, a distance between the quantum dots 231 may be reduced, and thus, by increasing quantum dot packing density of the emission layer 130 and improving arrangement uniformity of the quantum dots 231, the number of voids between the quantum dots 231 may be reduced, thereby preventing or substantially preventing a leakage current. In addition, thickness uniformity of the emission layer 130 may be improved to thereby improve luminescence efficiency of the light-emitting device 20, and a surface of the emission layer 130 may be flattened to improve a bonding force with respect to upper and lower layers (e.g., layers located directly above or directly below the emission layer 130).

Furthermore, when an upper layer of the emission layer 130 is formed by a solution process, by preventing or substantially preventing the emission layer 130 from being dissolved by an organic solvent (e.g., due to the formation of the cross-linked structure), a wide selection range of composition of a solution for forming the upper layer may be obtained.

Figure 3:
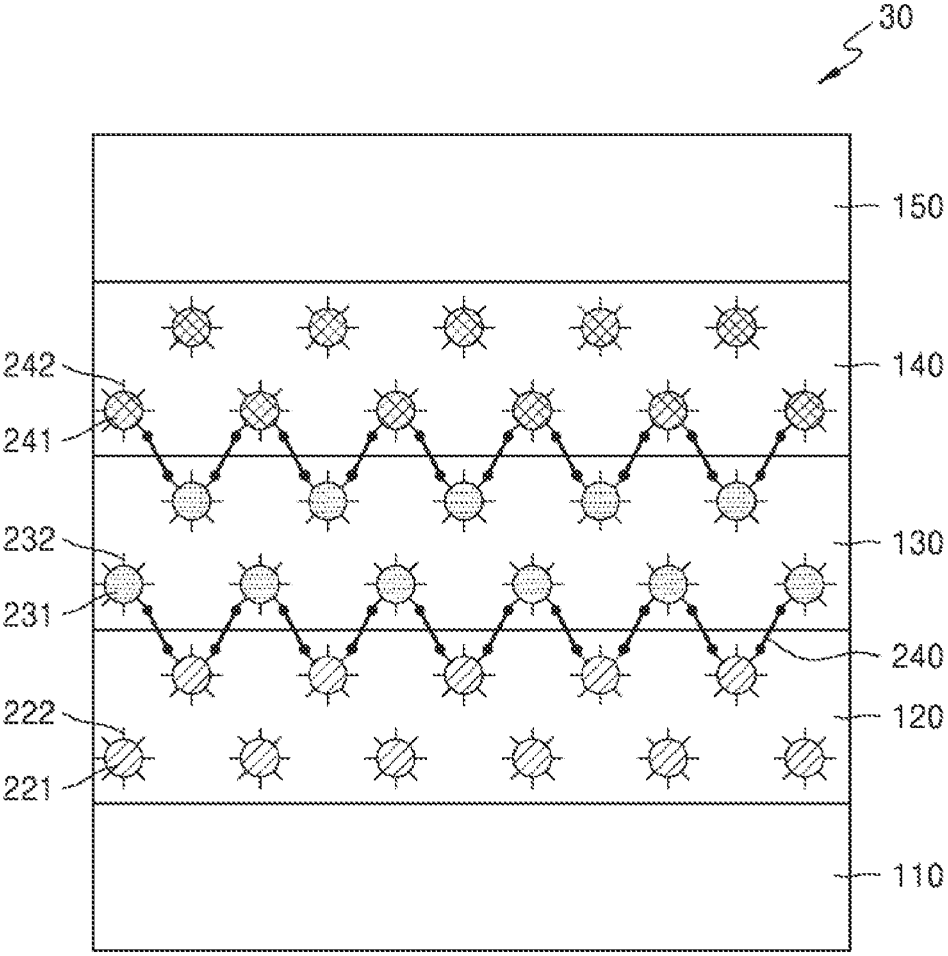
FIG. 3 is a schematic view of a light-emitting device according to another embodiment.

Description for FIG. 3

FIG. 3 is a schematic cross-sectional view of a light-emitting device 30 according to another embodiment.

The light-emitting device 30 may further include a second charge transport layer 140 located between the emission layer 130 and the second electrode 150 and including an inorganic nanoparticle 241 including a third ligand 242 bonded to a surface thereof.

The third ligand 242 may be understood by referring to the description of the second ligand 222 above, and the inorganic nanoparticle 241 may be understood by referring to the description of the inorganic nanoparticle 221 above.

An interface between the emission layer 130 and the second charge transport layer 140 may include a cross-link (e.g., a cross-linked structure) in which the first ligand 232 on the surface of the quantum dot 231 and the third ligand 242 on the surface of the inorganic nanoparticle 241 are linked by the cross-linking agent 240.

The inorganic nanoparticle 221 in the charge transport layer 120 and the inorganic nanoparticle 241 in the second charge transport layer 140 may be different from each other. One of the inorganic nanoparticle 221 and the inorganic nanoparticle 241 may include a metal oxide having hole-transporting characteristics, and the other one may include a metal oxide having electron-transporting characteristics.

In an embodiment, in the light-emitting device 30, the first electrode 110 may be an anode, the second electrode 150 may be a cathode, the charge transport layer 120 may be a hole transport layer, and the second charge transport layer 140 may be an electron transport layer. In this case, the inorganic nanoparticle 221 may include a p-type metal oxide, and the inorganic nanoparticle 241 may include an n-type metal oxide.

In one or more embodiments, in the light-emitting device 30, the first electrode 110 may be a cathode, the second electrode 150 may be an anode, the charge transport layer 120 may be an electron transport layer, and the second charge transport layer 140 may be a hole transport layer. In this case, the inorganic nanoparticle 221 may include an n-type metal oxide, and the inorganic nanoparticle 241 may include a p-type metal oxide.

Figure 4:
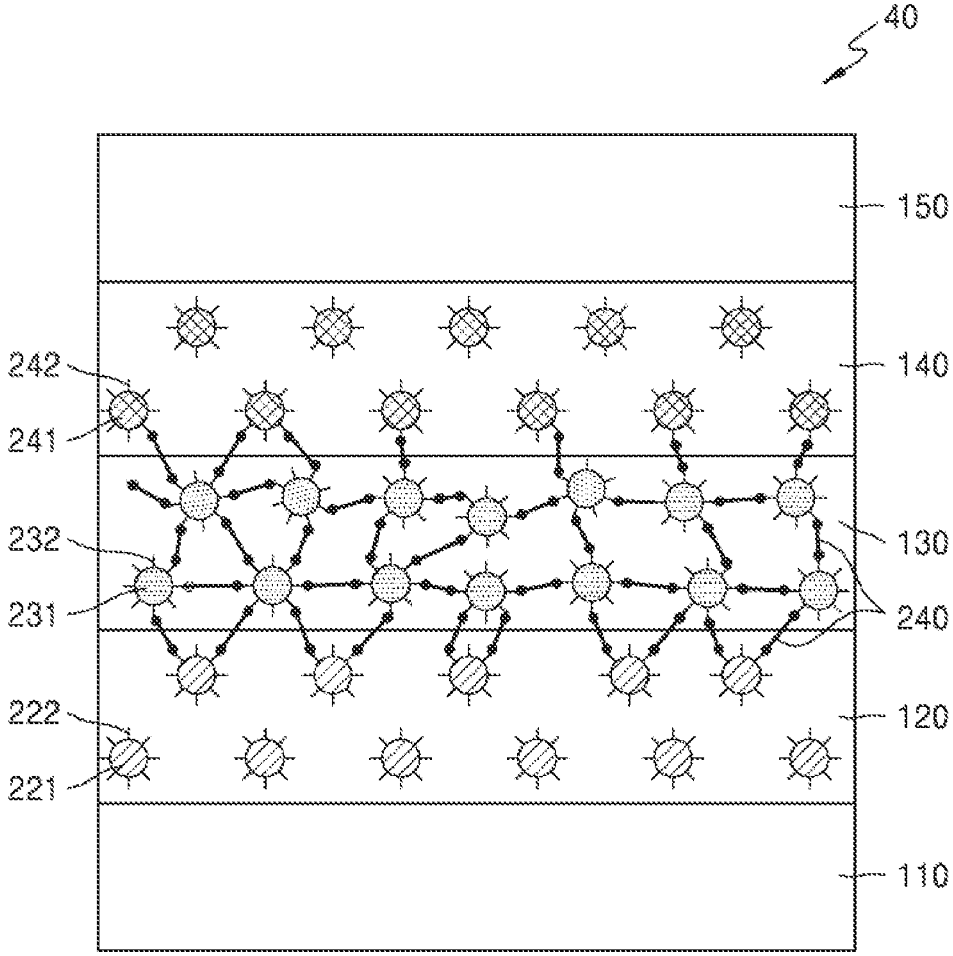
FIG. 4 is a schematic view of a light-emitting device according to another embodiment.

Description of FIG. 4

FIG. 4 is a schematic cross-sectional view of a light-emitting device 40 according to another embodiment.

The light-emitting device 40 includes a structure similar to that of the light-emitting device 30 described above, except that the emission layer 130 includes a cross-link (e.g., a cross-linked structure) in which a first ligand 232 on a surface of one quantum dot 231 and a first ligand 232 on a surface of another quantum dot 231 are linked by the cross-linking agent 240.

As such, because the emission layer 130 further includes the cross-link between the quantum dots 231, in light-emitting device 40, a leakage current may be prevented or substantially prevented, and luminescence efficiency may be improved.

Hole Transport Region

The hole transport region may have i) a single-layered structure consisting of a single layer consisting of a single material, ii) a single-layered structure consisting of a single layer including a plurality of different materials, or iii) a multi-layered structure having a plurality of layers including a plurality of different materials.

The hole transport region may include a hole injection layer, a hole transport layer, an emission auxiliary layer, an electron blocking layer, or any combination thereof.

In an embodiment, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers are stacked sequentially from the first electrode 110 in the respective stated order.

The hole transport region may include a compound represented by Formula 201, a compound represented by Formula 202, or any combination thereof:

Formula 201

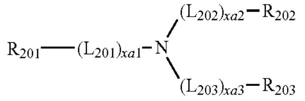

Formula 202

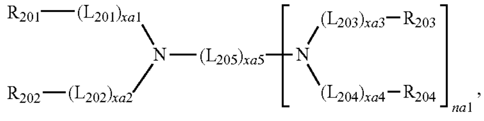

wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group and/or the like) unsubstituted or substituted with at least one $R_{10a}$ (for example, Compound HT16), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, each of Formulae 201 and 202 may include at least one of the groups represented by Formulae CY201 to CY217:

CY201

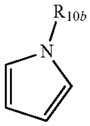

CY202

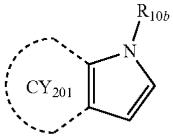

CY203

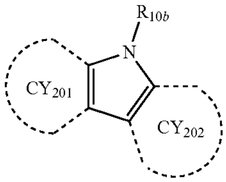

CY204

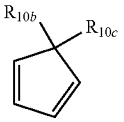

CY205

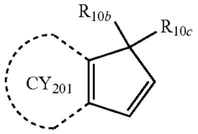

CY206

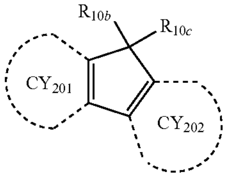

CY207

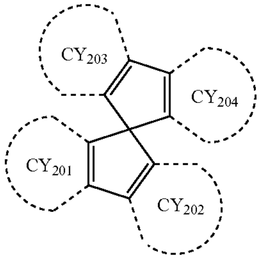

CY208

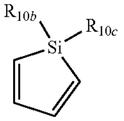

CY209

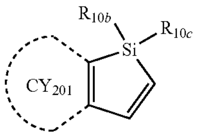

-continued

CY210

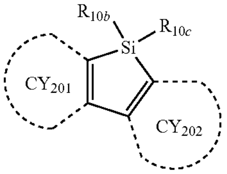

CY211

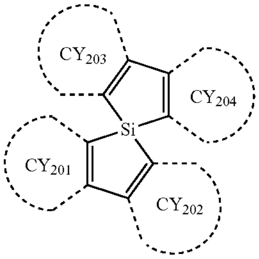

CY212

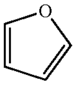

CY213

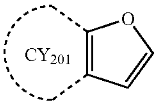

CY214

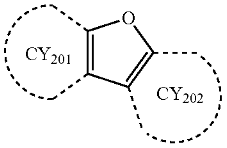

CY215

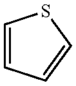

CY216

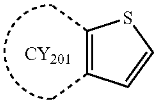

CY217

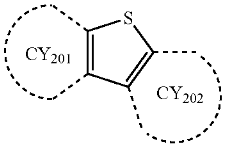

, wherein, in Formulae CY201 to CY217, $R_{10b}$ and $R_{10c}$ may each independently be the same as described in connection with $R_{10a}$, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, ring $CY_{201}$ to ring $CY_{204}$ in Formulae CY201 to CY217 may each independently be a benzene group, a naphthalene group, a phenanthrene group, or an anthracene group.

In one or more embodiments, each of Formulae 201 and 202 may include at least one of the groups represented by Formulae CY201 to CY203.

In one or more embodiments, Formula 201 may include at least one of the groups represented by Formulae CY201 to CY203 and at least one of the groups represented by Formulae CY204 to CY217.

In one or more embodiments, xa1 in Formula 201 may be 1, $R_{201}$ may be a group represented by one of Formulae CY201 to CY203, xa2 may be 0, and $R_{202}$ may be a group represented by one of Formulae CY204 to CY207.

In one or more embodiments, each of Formulae 201 and 202 may not include any of the groups represented by Formulae CY201 to CY203.

In one or more embodiments, each of Formulae 201 and 202 may not include any of the groups represented by Formulae CY201 to CY203, and may include at least one of the groups represented by Formulae CY204 to CY217.

In one or more embodiments, each of Formulae 201 and 202 may not include any of the groups represented by Formulae CY201 to CY217.

In an embodiment, the hole transport region may include one of Compounds HT1 to HT44, m-MTDATA, TDATA, 2-TNATA, NPB(NPD), β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1

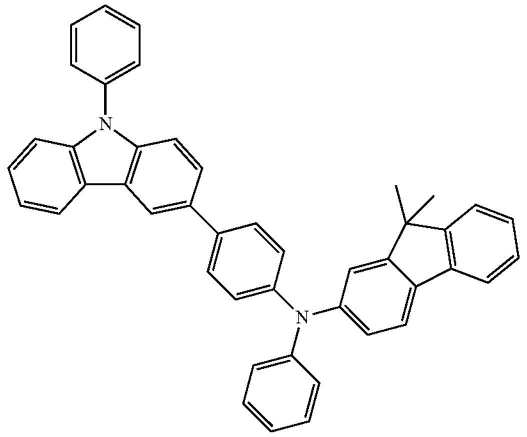

HT2

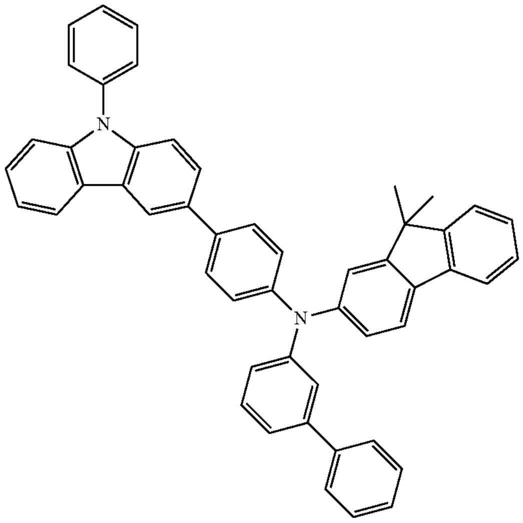

HT3

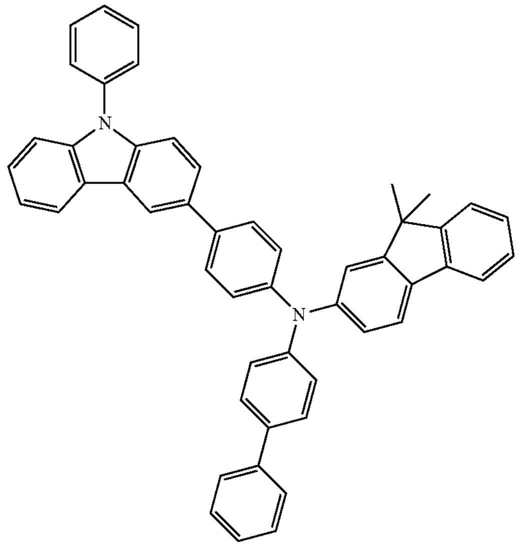

HT4

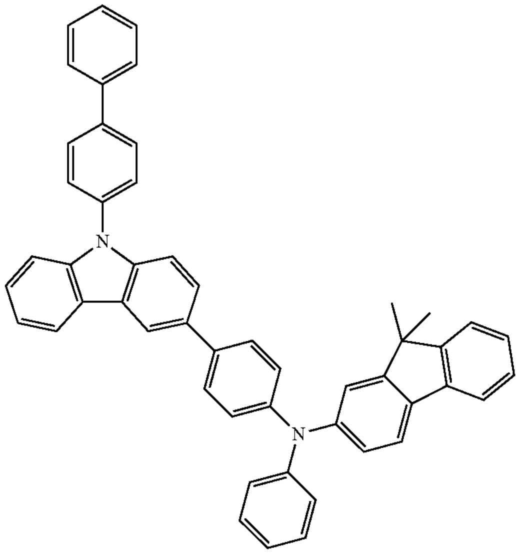

-continued
HT5
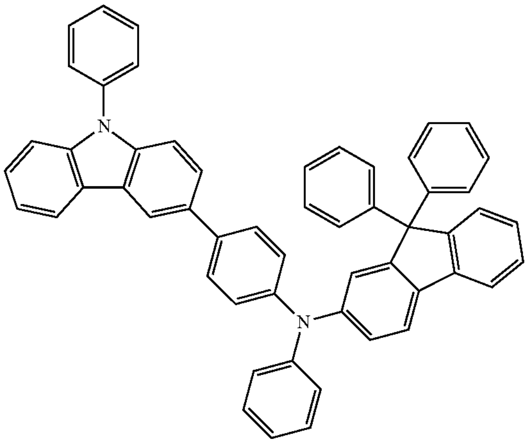
HT6
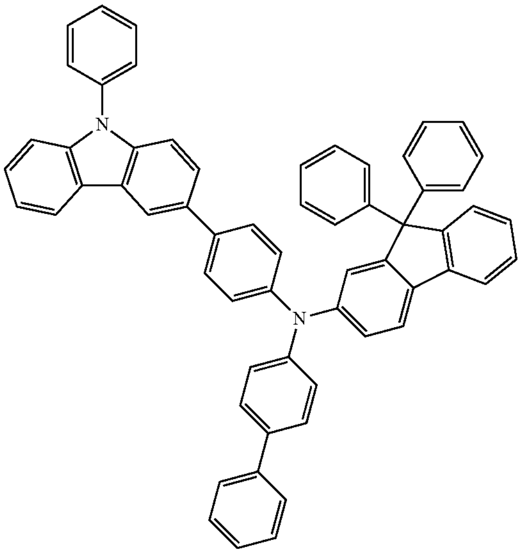
HT7
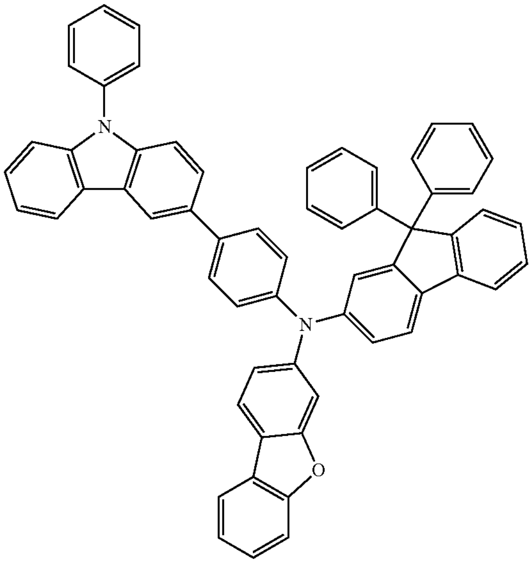
HT8
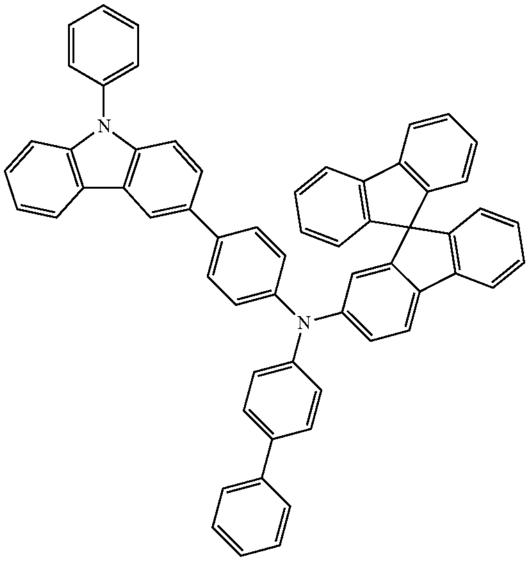

-continued
HT9
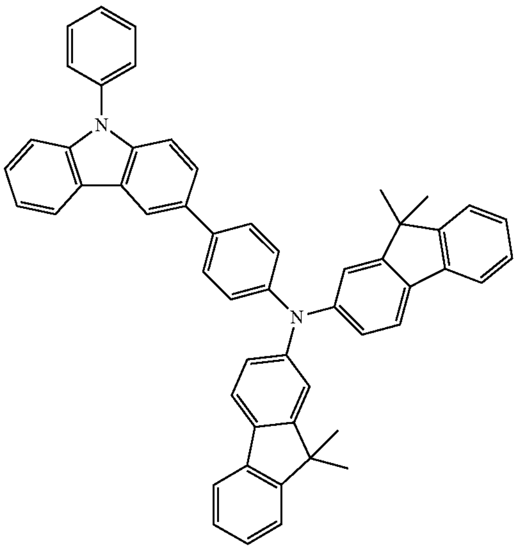
HT10
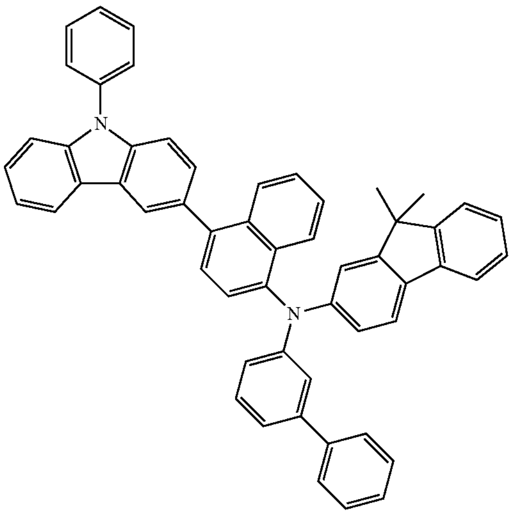
HT11
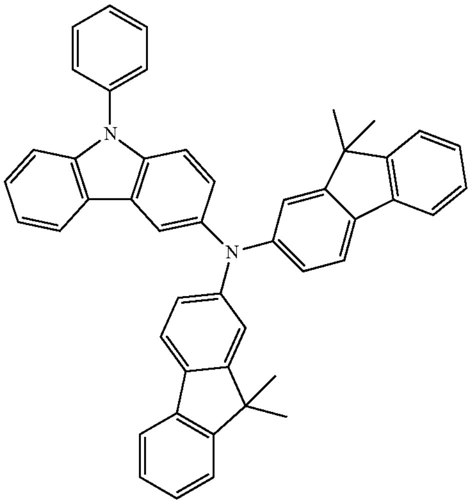
HT12
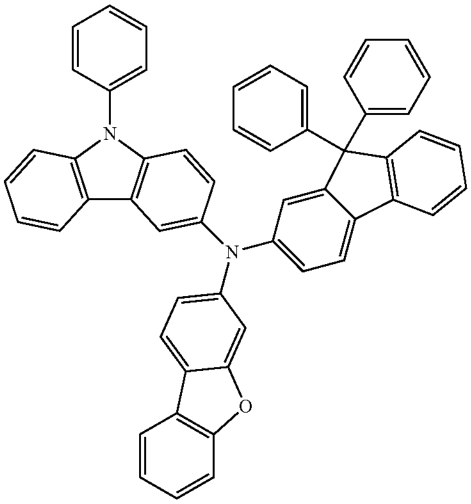
HT13
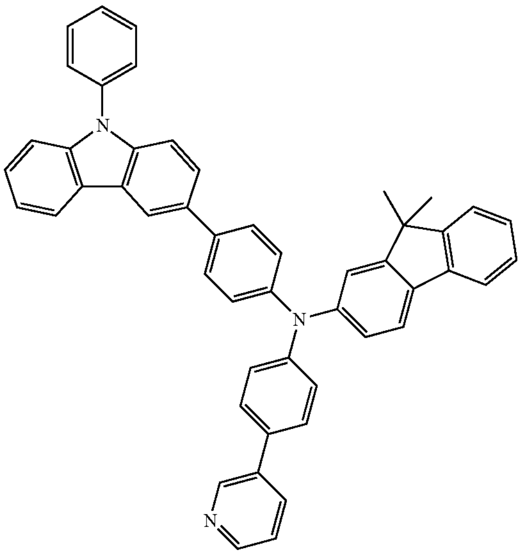
HT14
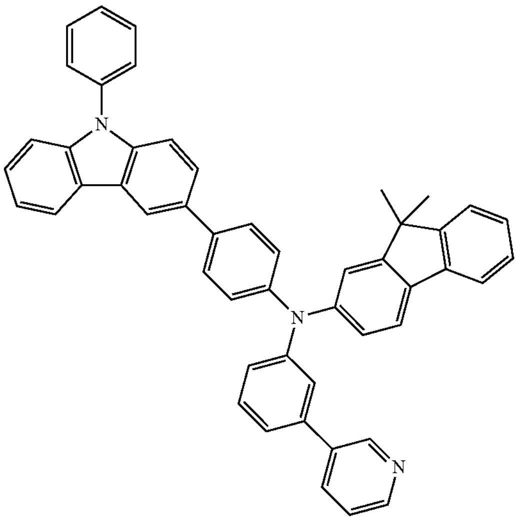

-continued
HT15
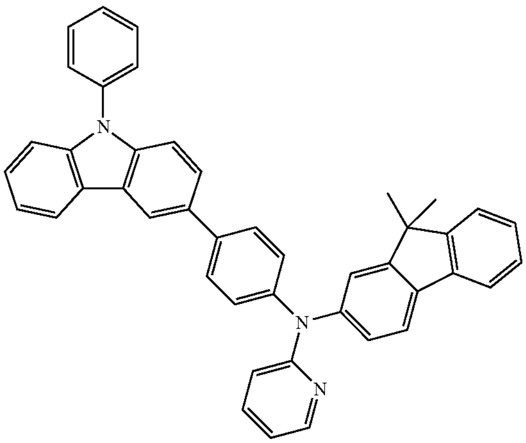
HT16
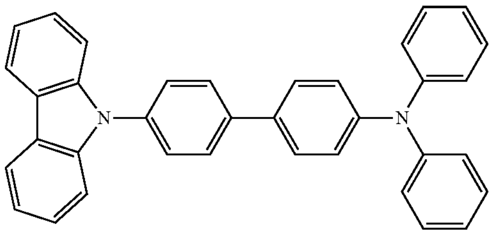
HT17
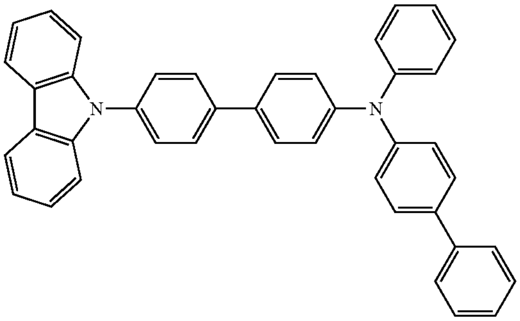
HT18
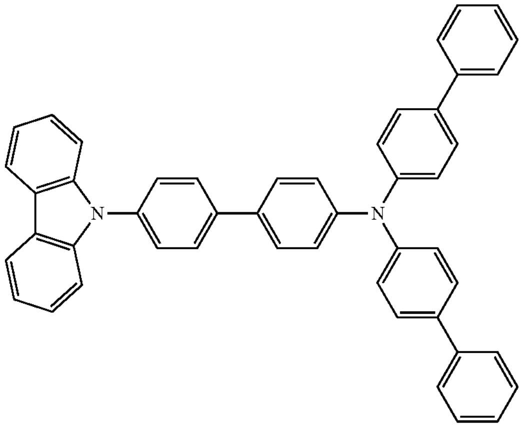
HT19
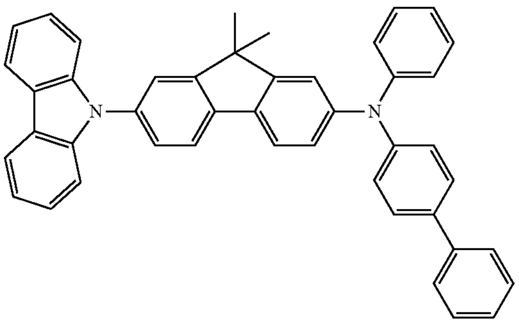
HT20
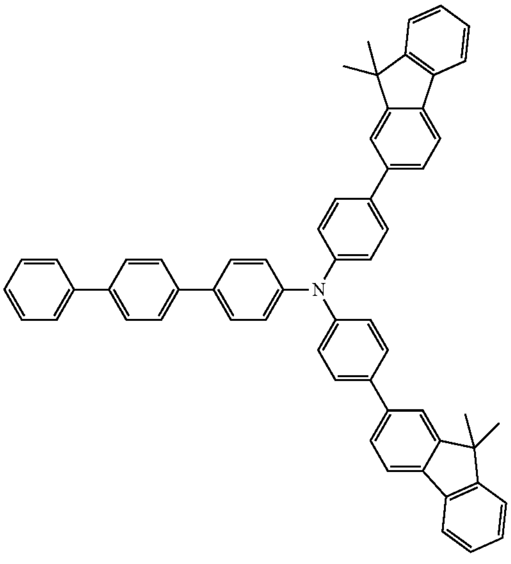

-continued
HT21
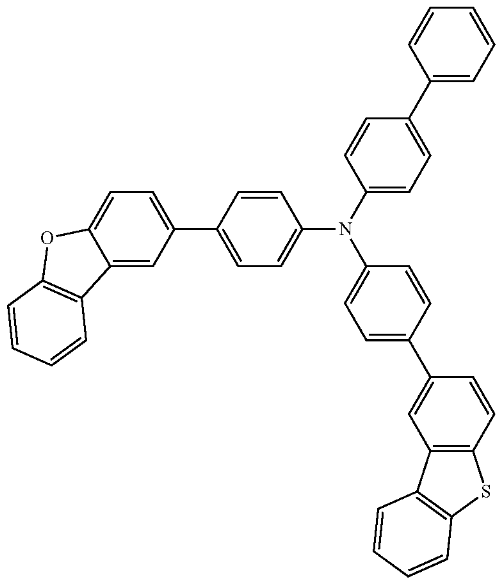
HT22
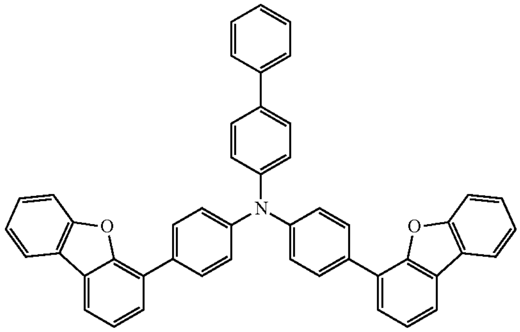
HT23
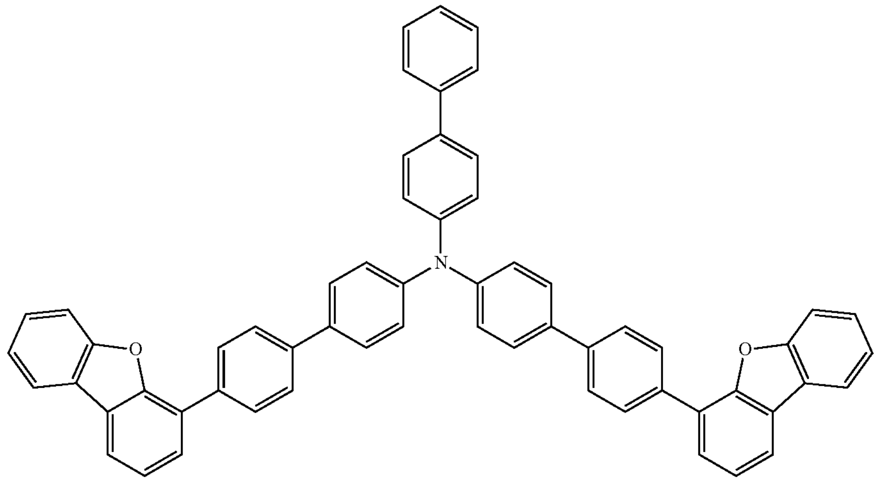
HT24
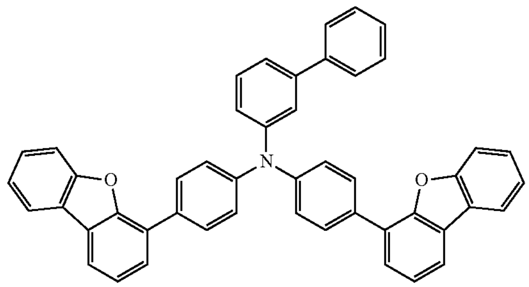
HT25
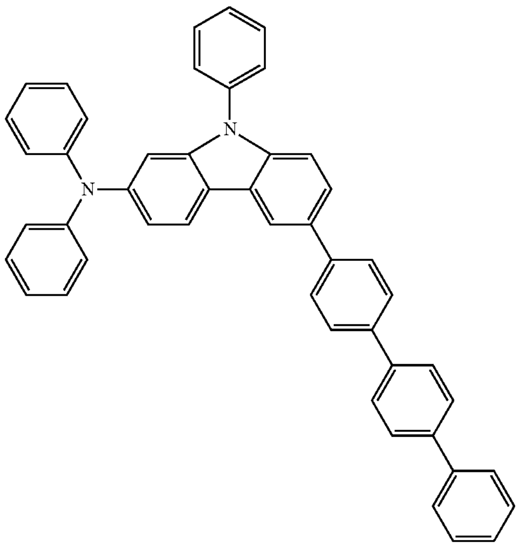

-continued
HT26
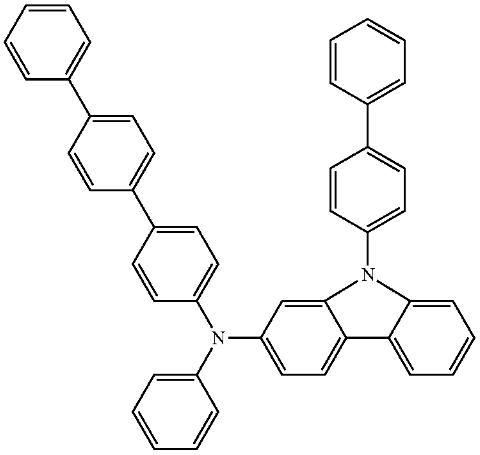
HT27
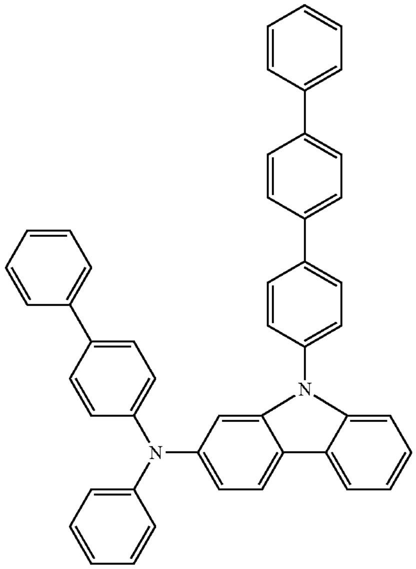
HT28
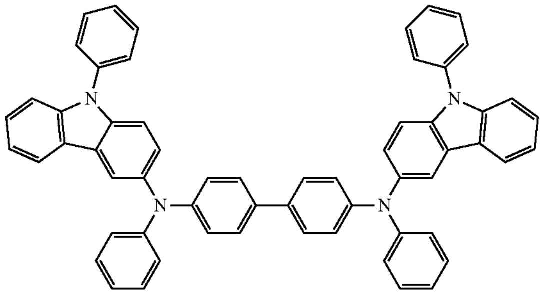
HT29
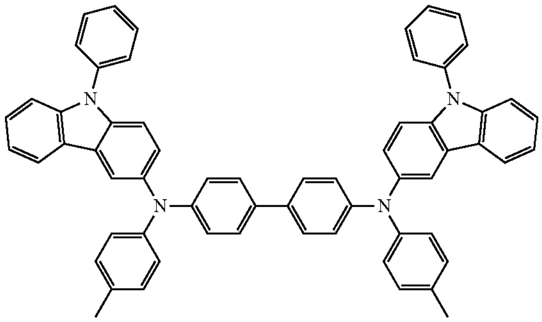
HT30
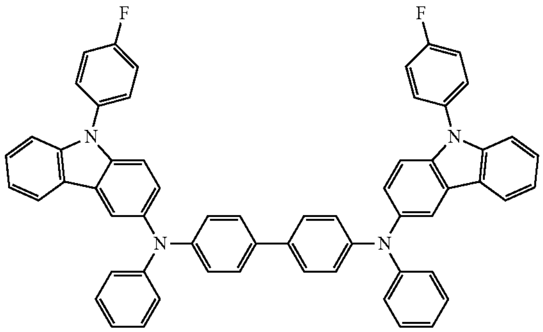
HT31
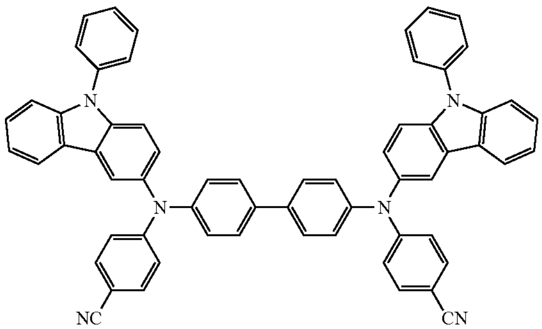

-continued
HT32
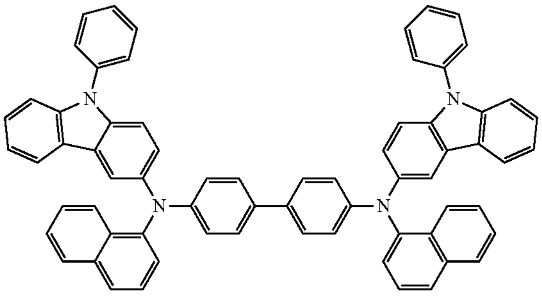
HT33
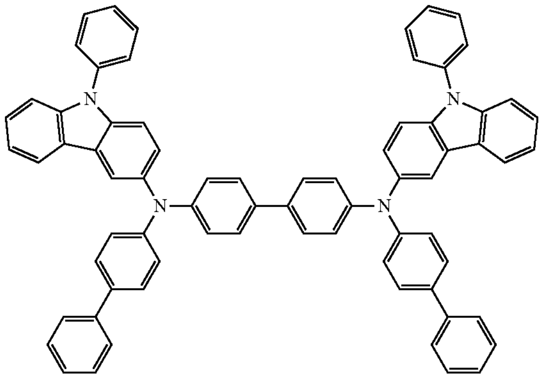
HT34
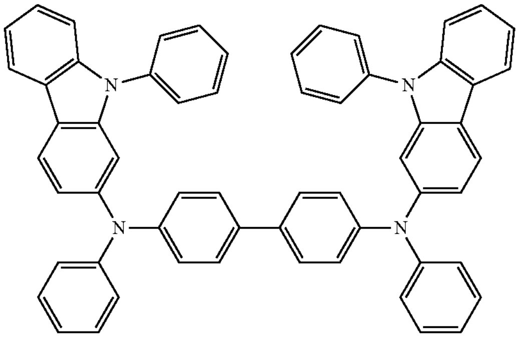
HT35
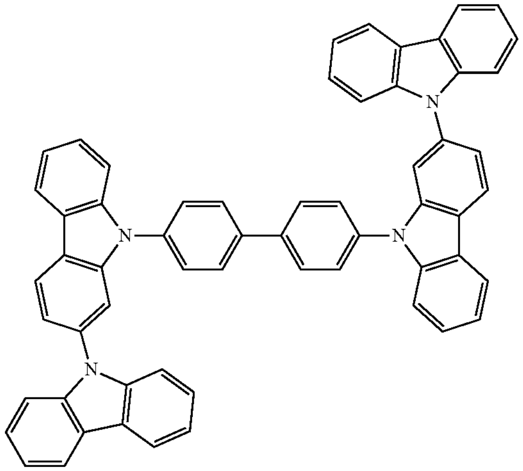
HT36
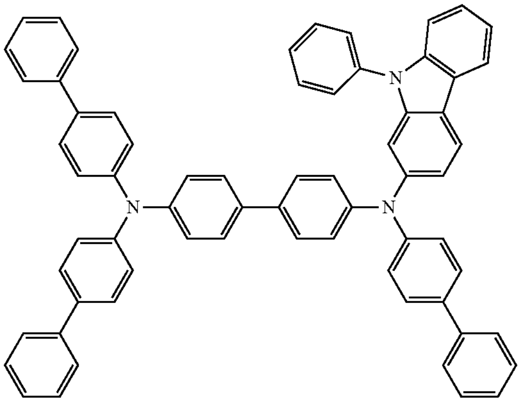
HT37
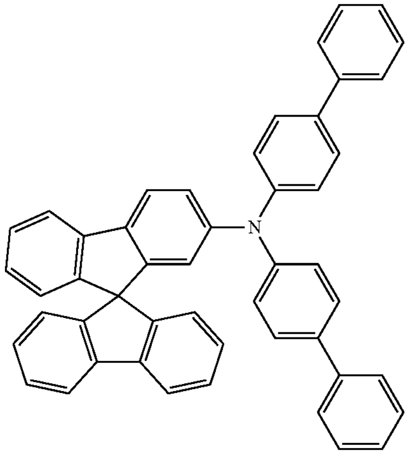

-continued
HT38
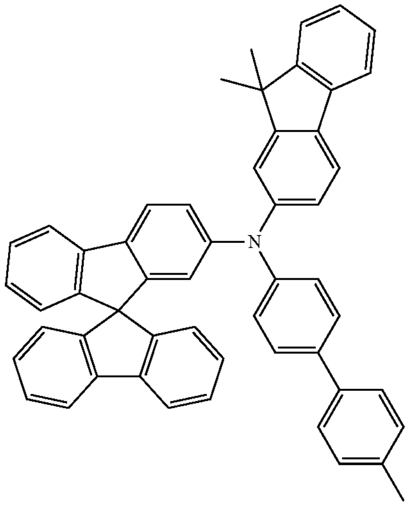
HT39
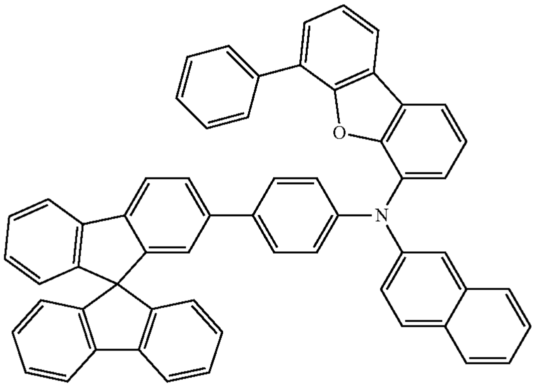
HT40
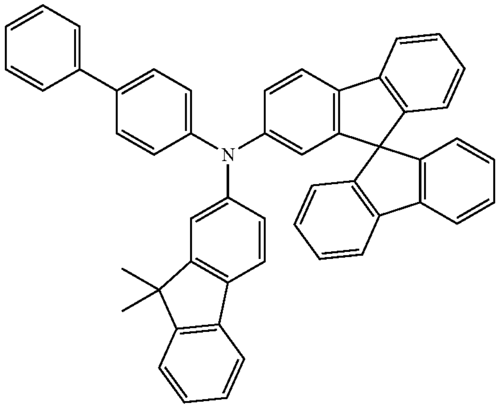
HT41
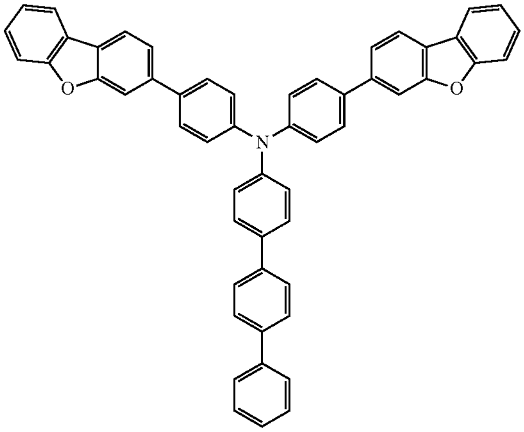
HT42
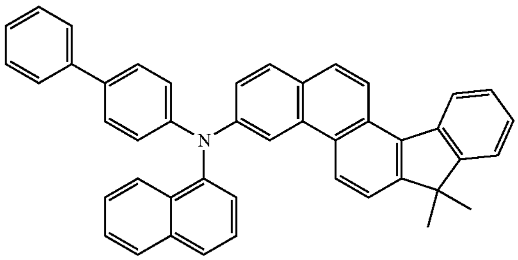
HT43
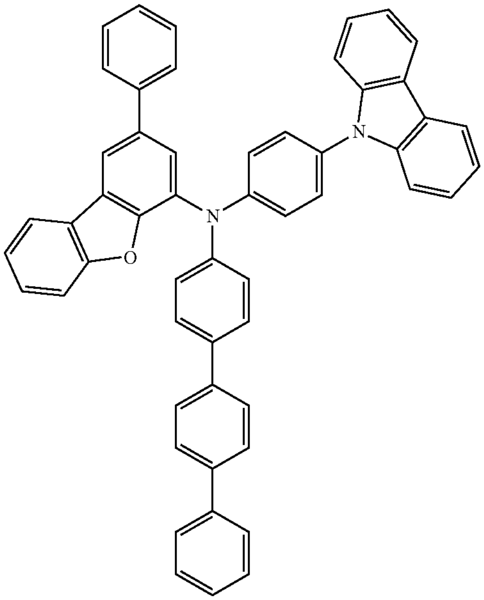

-continued
HT44
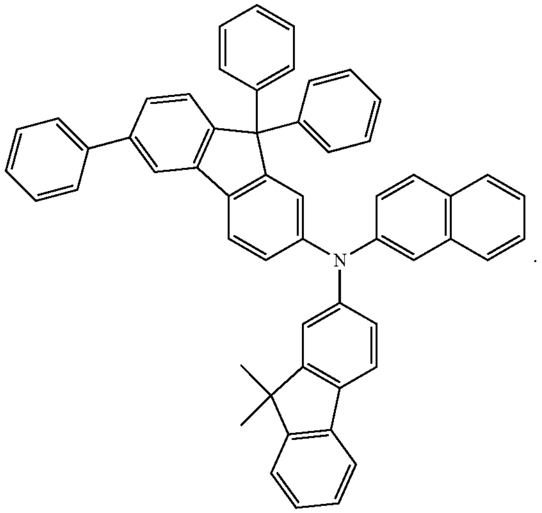
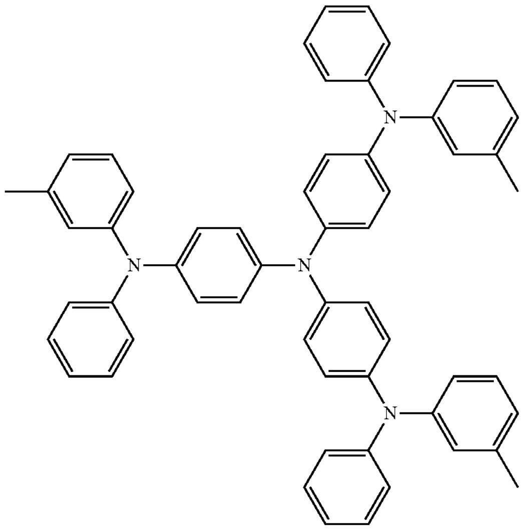
m-MTDATA
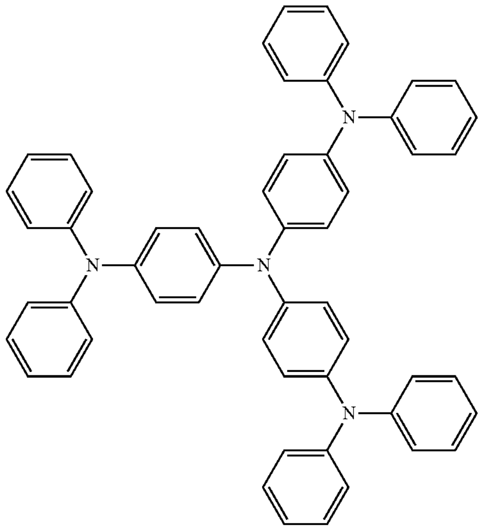
TDATA

-continued
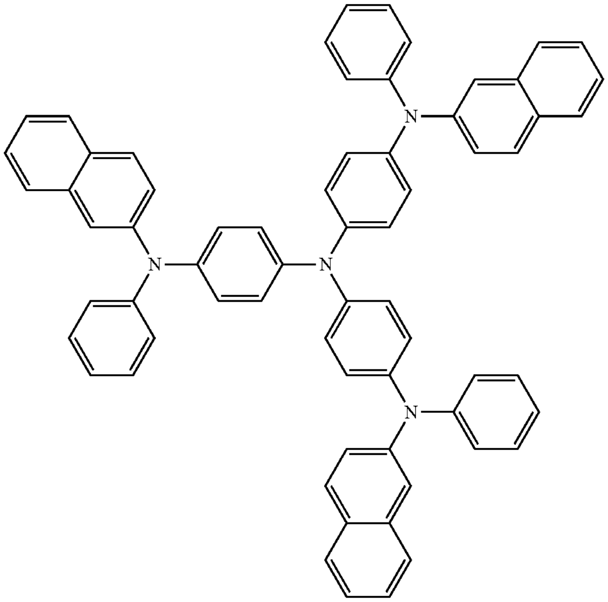
2-TNATA
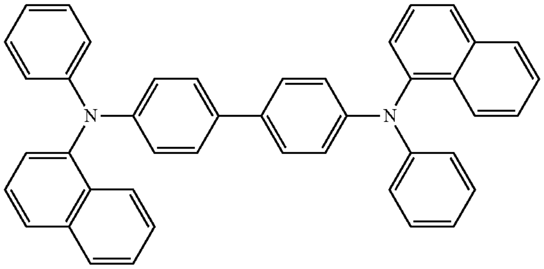
NPB
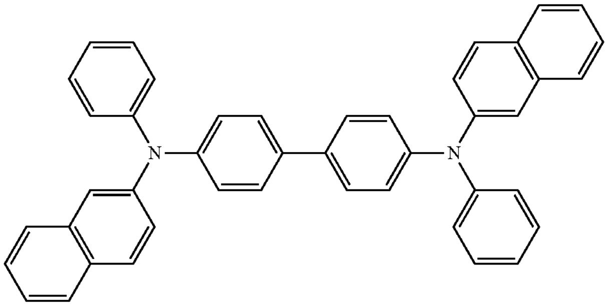
β-NPB
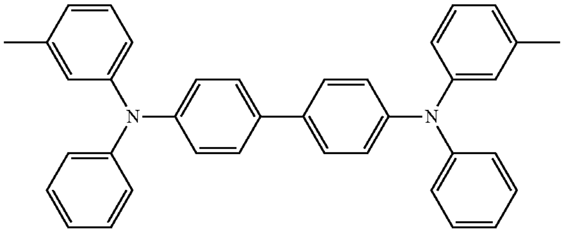
TPD
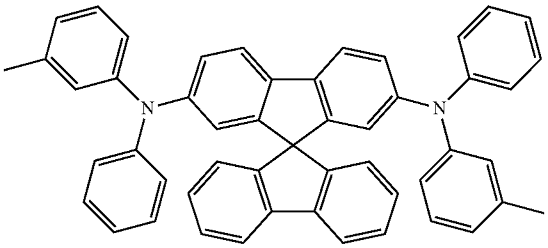
Spiro-TPD -continued

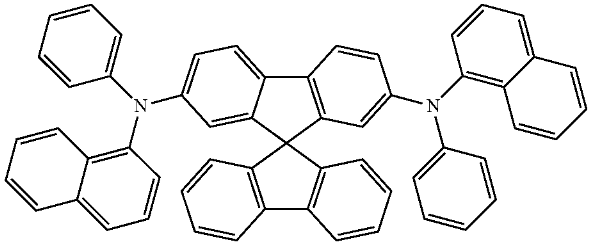

Spiro-NPB

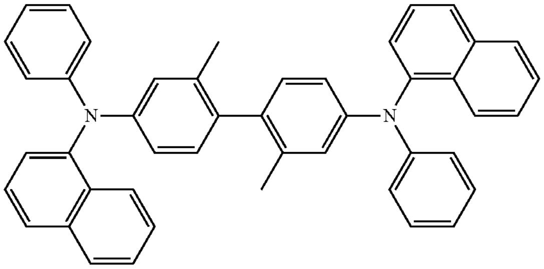

methylated-NPB

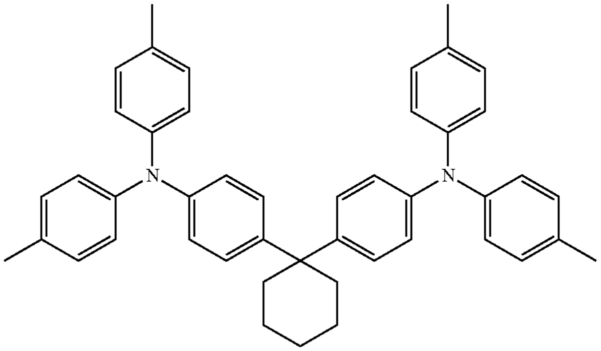

TAPC

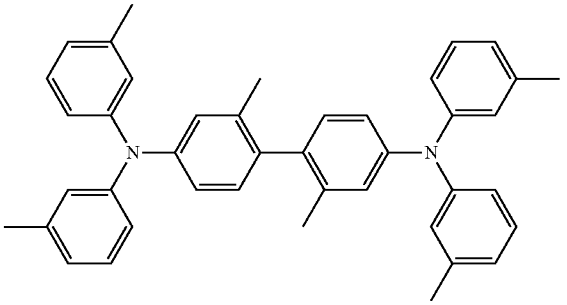

HMTPD

A thickness of the hole transport region may be in a range of about 50 Å to about 10,000 Å, for example, about 100 Å to about 4,000 Å. When the hole transport region includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer 130, and the electron blocking layer may block or reduce the flow of electrons from an electron transport region. The emission auxiliary layer and the electron blocking layer may include the materials as described above.

p-Dopant

The hole transport region may further include, in addition to the aforementioned materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

In an embodiment, the lowest unoccupied molecular orbital (LUMO) energy level of the p-dopant may be −3.5 eV or less.

In an embodiment, the p-dopant may include a quinone derivative, a cyano group-containing compound, a compound containing element EL1 and element EL2, or any combination thereof.

Examples of the quinone derivative may include TCNQ, F4-TCNQ, and the like.

Examples of the cyano group-containing compound may include HAT-CN, a compound represented by Formula 221 below, and the like.

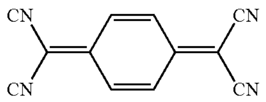

TCNQ

-continued

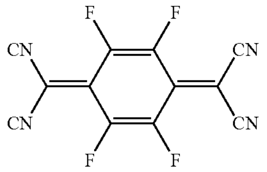

F4-TCNQ

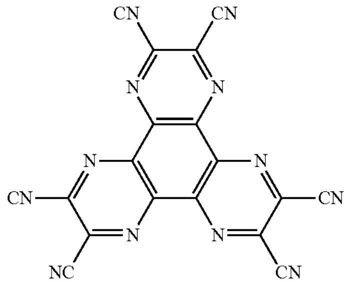

HAT-CN

Formula 221

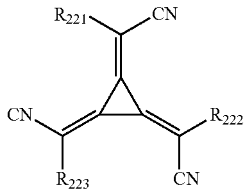

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or a combination thereof, and element EL2 may be a non-metal, a metalloid, or a combination thereof.

Examples of the metal may include: an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid may include silicon (Si), antimony (Sb), and tellurium (Te).

Examples of the non-metal may include oxygen (O) and halogen (for example, F, Cl, Br, I, etc.).

In an embodiment, examples of the compound containing element EL1 and element EL2 may include a metal oxide, a metal halide (for example, metal fluoride, metal chloride, metal bromide, and/or metal iodide), a metalloid halide (for example, metalloid fluoride, metalloid chloride, metalloid bromide, and/or metalloid iodide), a metal telluride, or any combination thereof.

Examples of the metal oxide may include tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), and rhenium oxide (for example, $ReO_3$, etc.).

Examples of the metal halide may include alkali metal halide, alkaline earth metal halide, transition metal halide, post-transition metal halide, and lanthanide metal halide.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may include titanium halide (for example, $TiF_4$, $TiCl_4$, $TiBr_4$, $TiI_4$, etc.), zirconium halide (for example, $ZrF_4$, $ZrCl_4$, $ZrBr_4$, $ZrI_4$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, $ReI_2$, etc.), iron halide (for example, $FeF_2$, $FeCl_2$, $FeBr_2$, $FeI_2$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtCl_2$, $PtBr_2$, $PtI_2$, etc.), copper halide (for example, CuF, CuCl, CuBr, CuI, etc.), silver halide (for example, AgF, AgCl, AgBr, AgI, etc.), and gold halide (for example, AuF, AuCl, AuBr, AuI, etc.).

Examples of the post-transition metal halide may include zinc halide (for example, $ZnF_2$, $ZnCl_2$, $ZnBr_2$, $ZnI_2$, etc.), indium halide (for example, $InI_3$, etc.), and tin halide (for example, $SnI_2$, etc.).

Examples of the lanthanide metal halide may include YbF, $YbF_2$, $YbF_3$, $SmF_3$, YbCl, $YbCl_2$, $YbCl_3$, $SmCl_3$, YbBr, $YbBr_2$, $YbBr_3$, $SmBr_3$, YbI, $YbI_2$, $YbI_3$, and $SmI_3$.

Examples of the metalloid halide may include antimony halide (for example, $SbCl_5$, etc.).

Examples of the metal telluride may include alkali metal telluride (for example, $Li_2Te$, $Na_2Te$, $K_2Te$, $Rb_2Te$, $Cs_2Te$, etc.), alkaline earth metal telluride (for example, BeTe, MgTe, CaTe, SrTe, BaTe, etc.), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), post-transition metal telluride (for example, ZnTe, etc.), and lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer 130

The emission layer 130 includes the quantum dot 231 and the first ligand 232 as described above.

Electron Transport Region

The electron transport region may have i) a single-layered structure consisting of a single layer consisting of a single material, ii) a single-layered structure consisting of a single layer including a plurality of different materials, or iii) a multi-layered structure having a plurality of layers including a plurality of different materials.

The electron transport region may include a buffer layer, a hole blocking layer, an electron control layer, an electron transport layer, an electron injection layer, or any combination thereof.

In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers are sequentially stacked from the emission layer 130 in the respective stated order.

The electron transport region (for example, the buffer layer, the hole blocking layer, the electron control layer, and/or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601:

$$[Ar_{601}]_{xe11}\text{-}[(L_{601})_{xe1}\text{-}R_{601}]_{xe21}$$ Formula 601 wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{601})(Q_{602})(Q_{603})$, —$C(=O)(Q_{601})$, —$S(=O)_2(Q_{601})$, or —$P(=O)(Q_{601})(Q_{602})$, $Q_{601}$ to $Q_{603}$ may each independently be the same as described in connection with the following $Q_1$, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}$(s) may be linked to each other via a single bond.

In one or more embodiments, $Ar_{601}$ in Formula 601 may be a substituted or unsubstituted anthracene group.

In one or more embodiments, the electron transport region may include a compound represented by Formula 601-1:

Formula 601-1

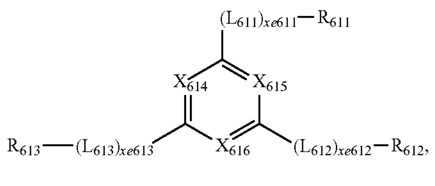

wherein, in Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, or any combination thereof:

ET1

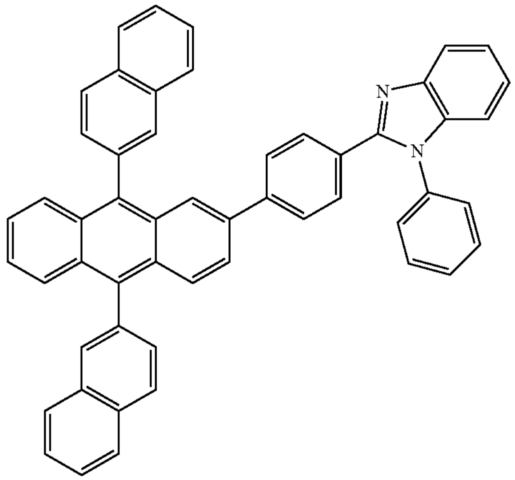

ET2
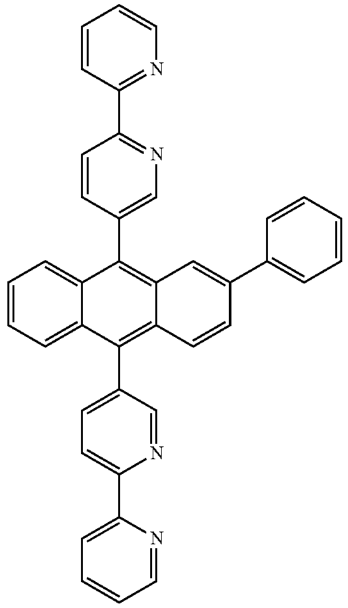
ET3
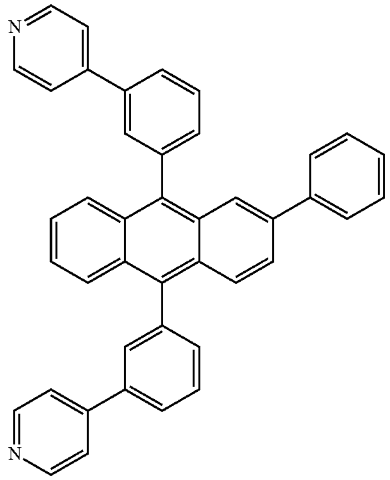
ET4
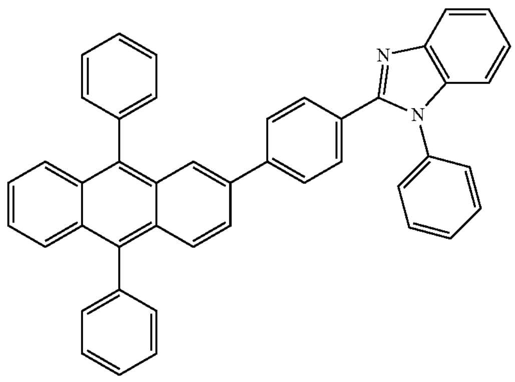
ET5
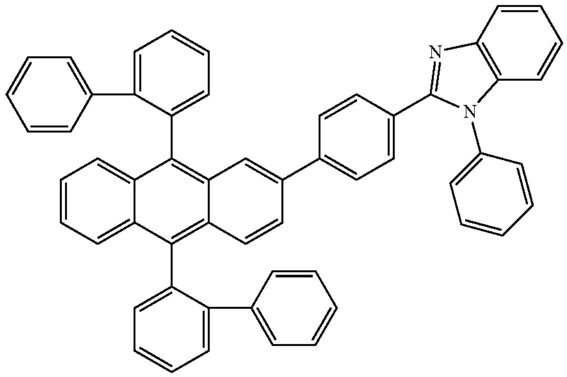
ET6
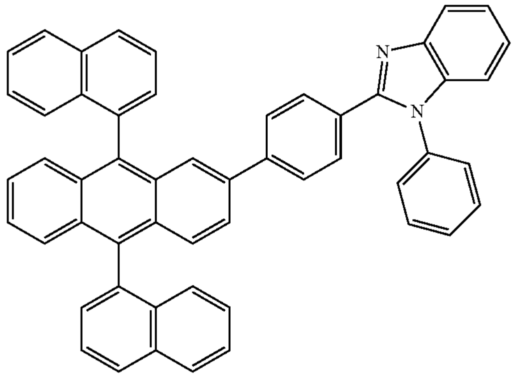
ET7
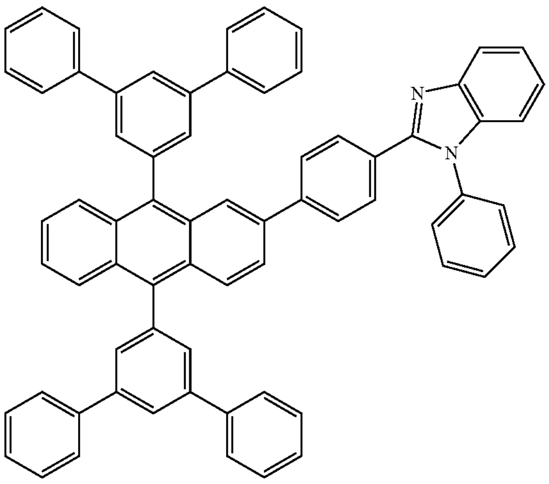

-continued
ET8
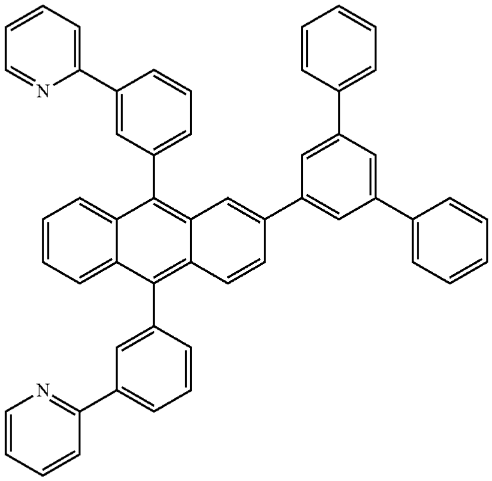
ET9
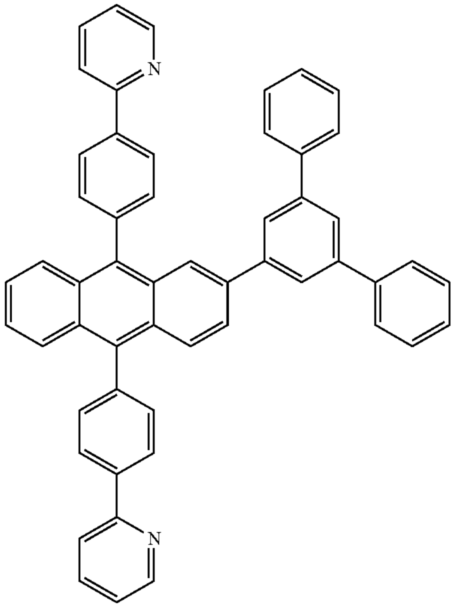
-continued
ET10
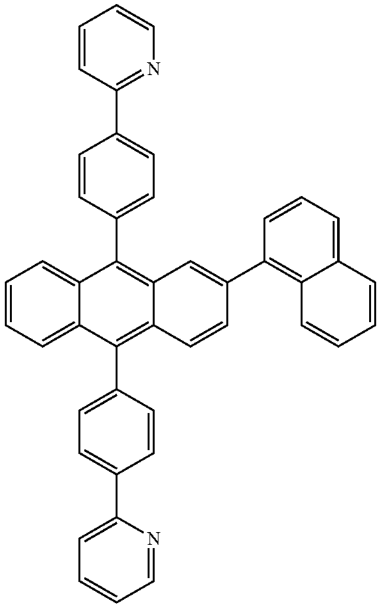
ET11
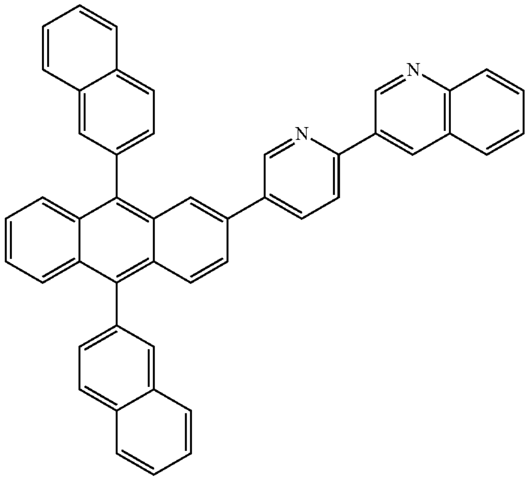
ET12
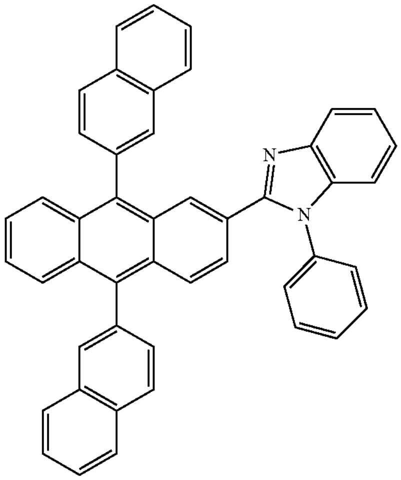

-continued
ET13
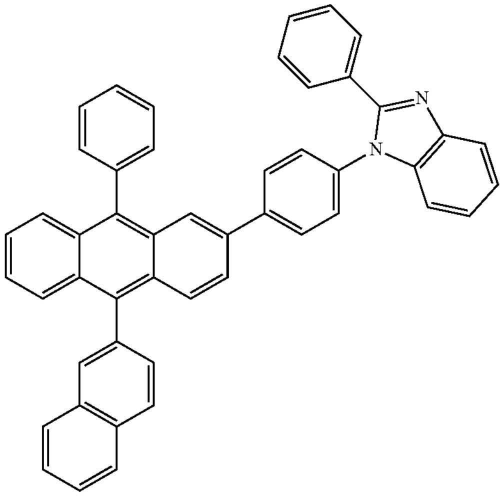
ET14
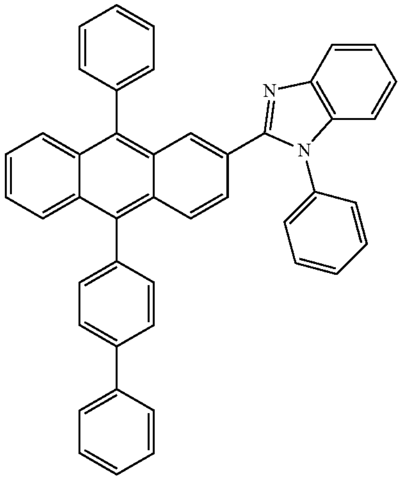
ET15
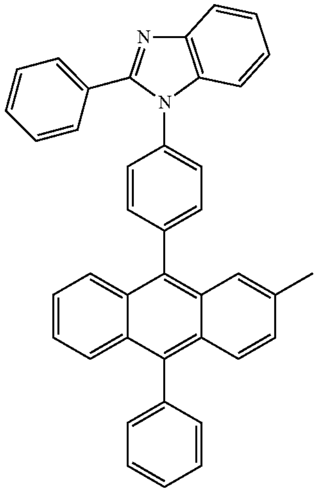
-continued
ET16
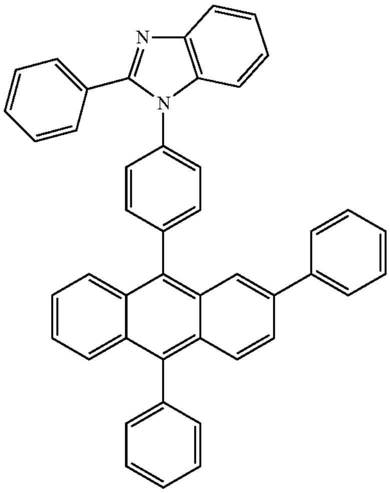
ET17
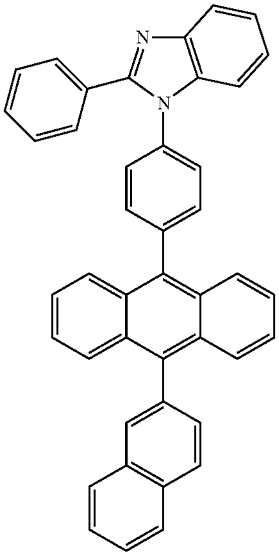
ET18
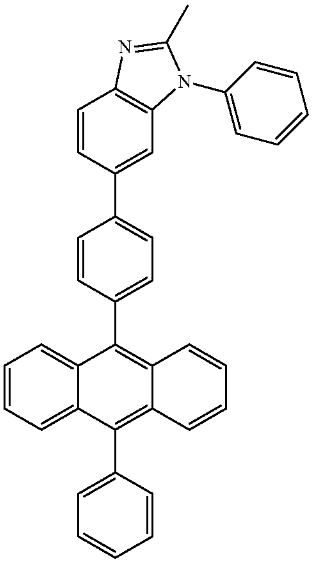

-continued
ET19
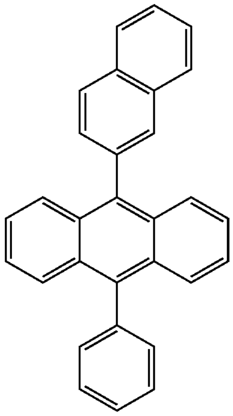
ET20
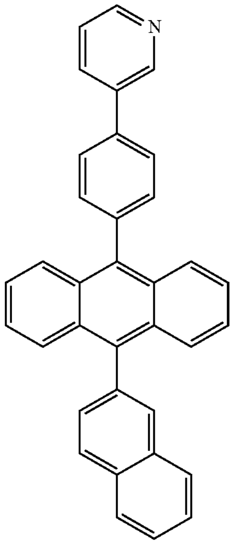
ET21
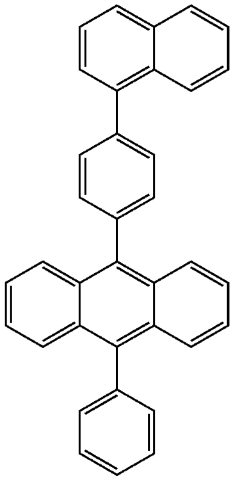
-continued
ET22
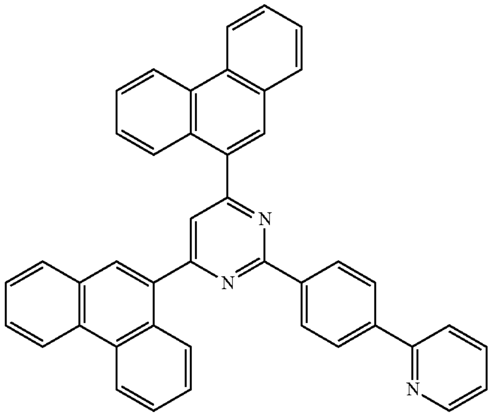
ET23
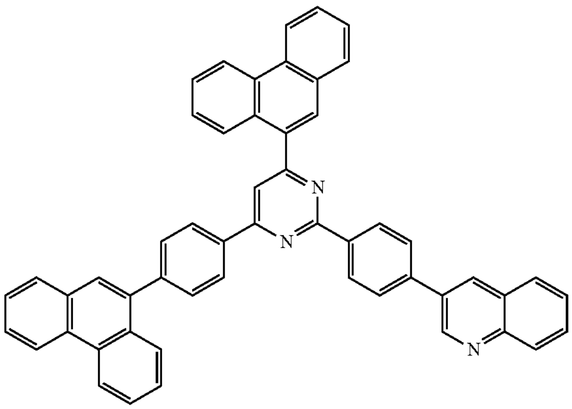
ET24
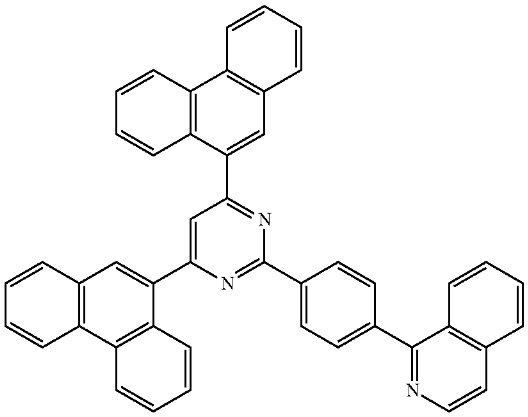

-continued
ET25
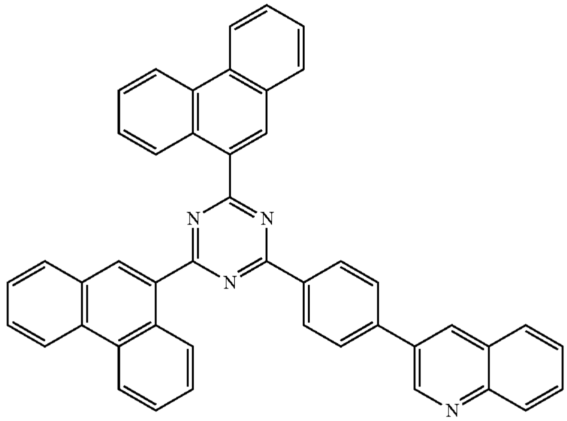
ET26
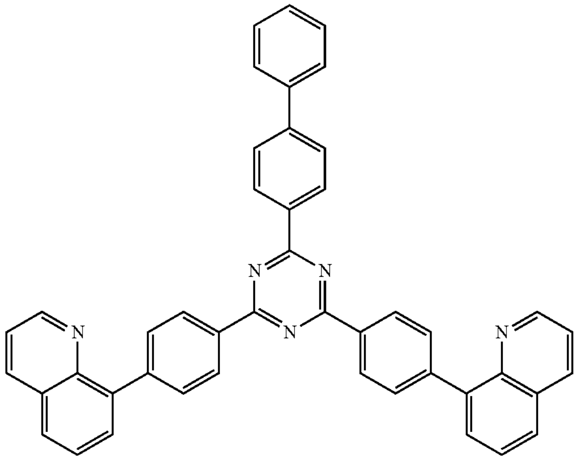
ET27
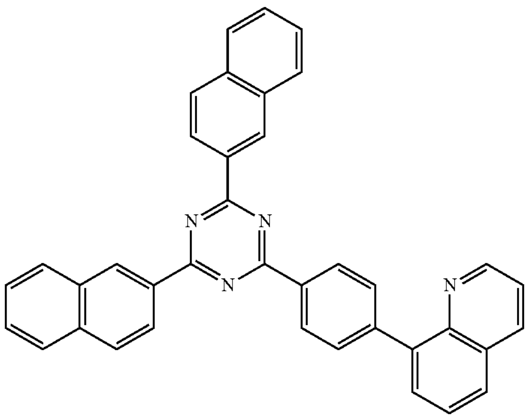
-continued
ET28
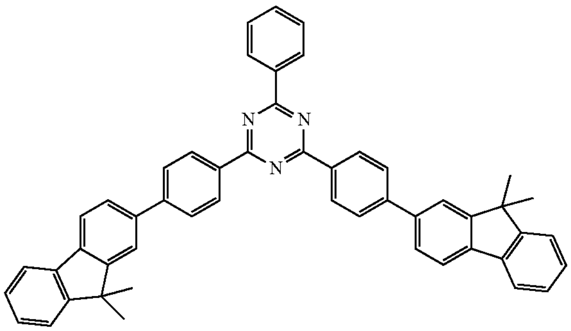
ET29
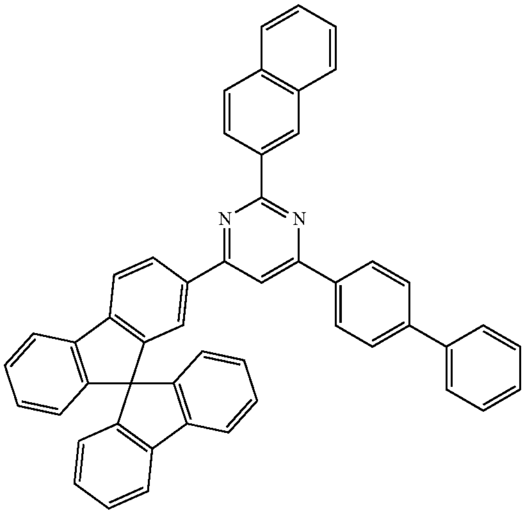
ET30
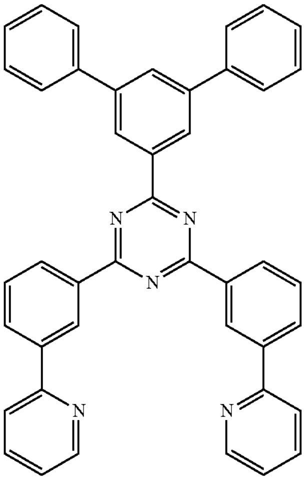

-continued
ET31
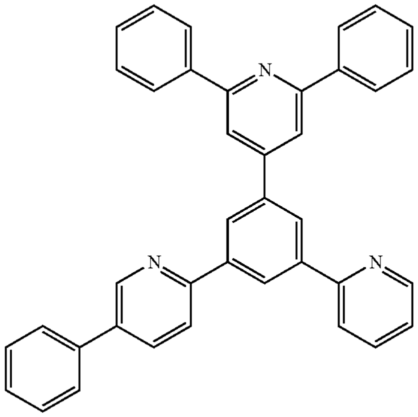
ET32
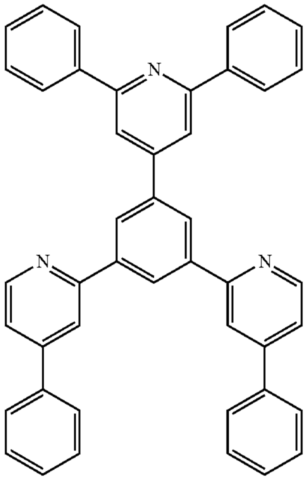
ET33
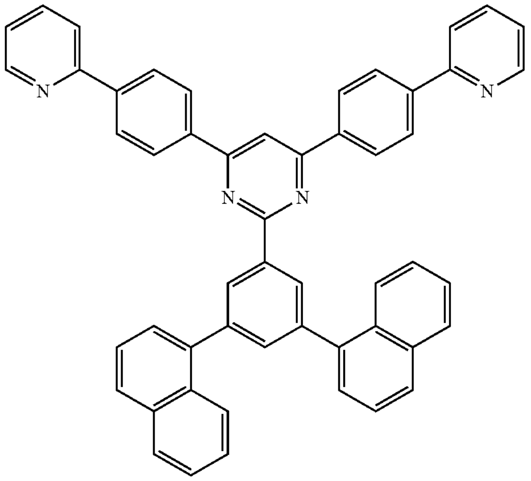
-continued
ET34
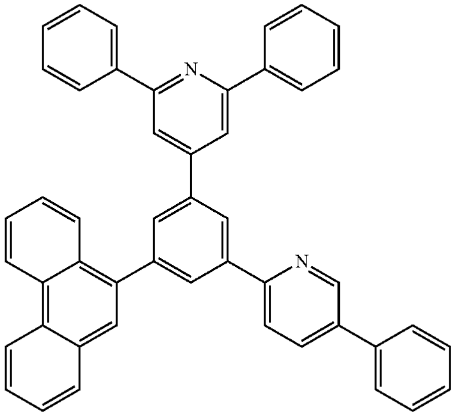
ET35
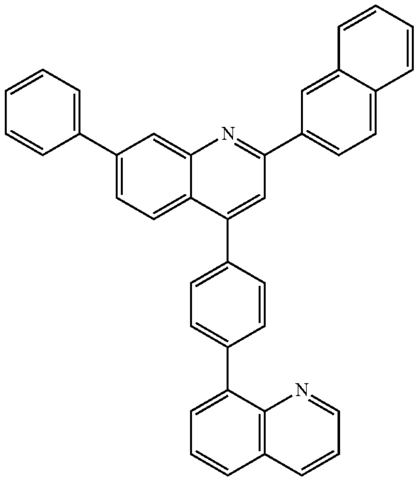
ET36
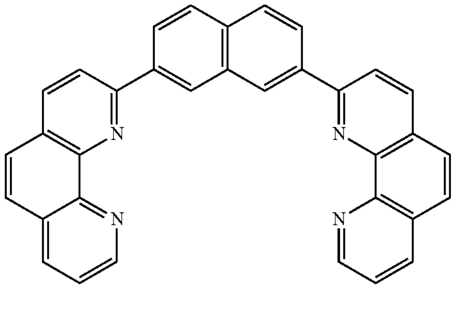
ET37
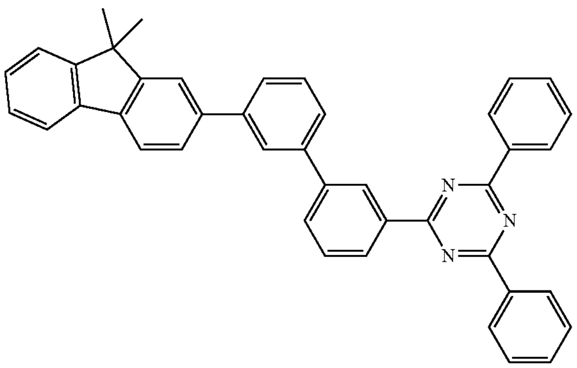

-continued
ET38
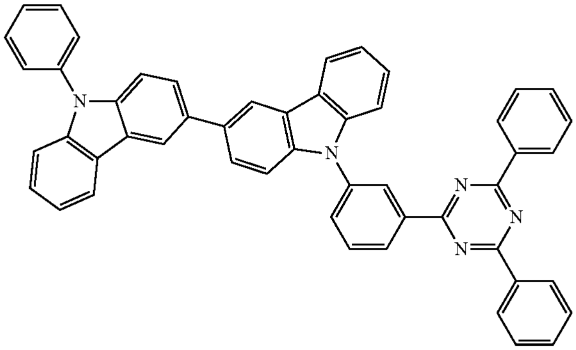
ET39
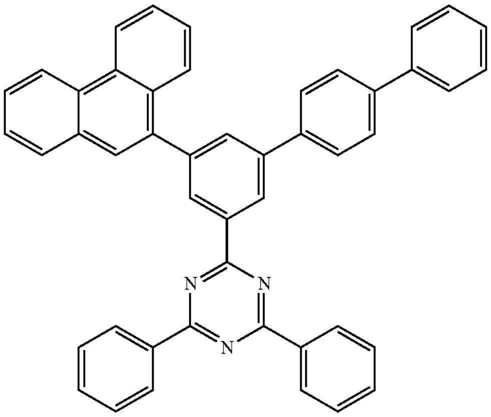
ET40
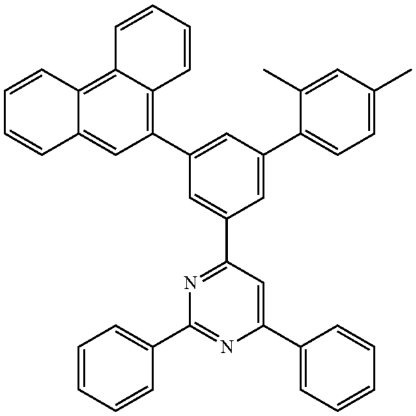
-continued
ET41
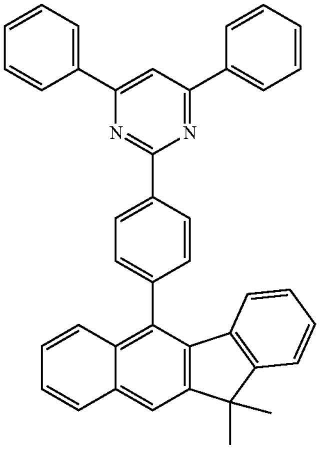
ET42
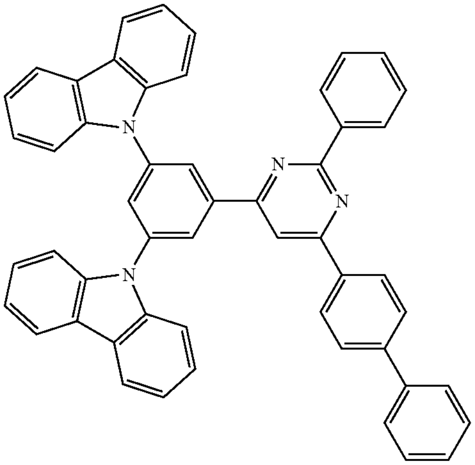
ET43
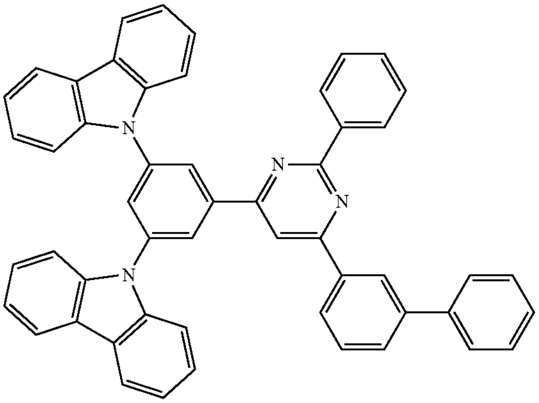

-continued

ET44

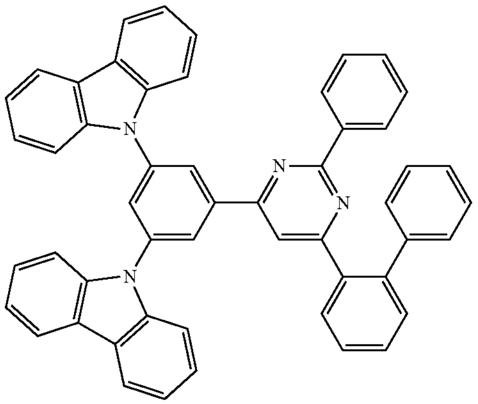

ET45

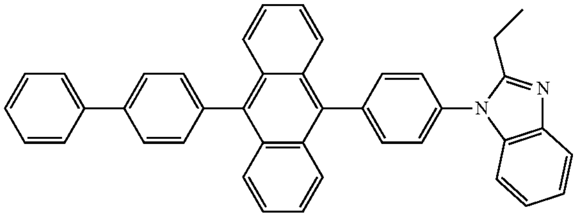

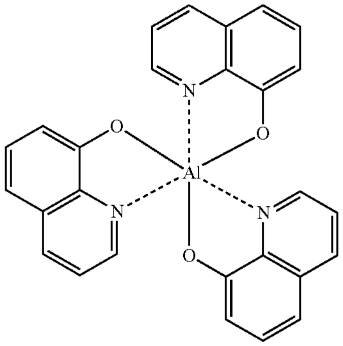

Alq3

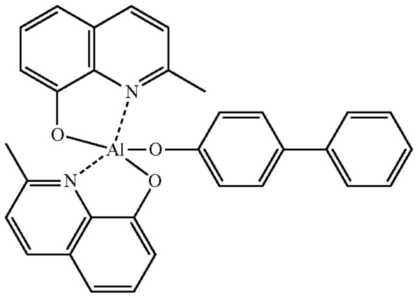

BAlq

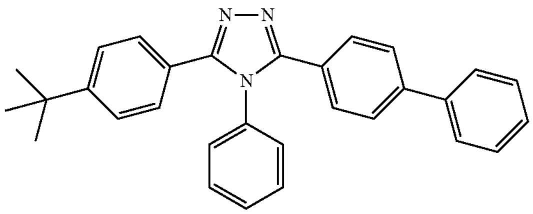

TAZ

-continued

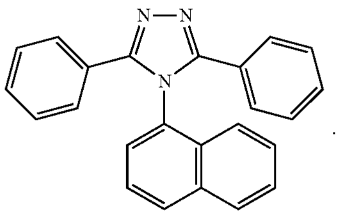

NTAZ

A thickness of the electron transport region may be from about 100 Å to about 5,000 Å, for example, from about 100 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be from about 20 Å to about 1,000 Å, for example, about 30 Å to about 300 Å, and a thickness of the electron transport layer may be from about 100 Å to about 1,000 Å, for example, about 150 Å to about 500 Å. When the thicknesses of the buffer layer, the hole blocking layer, the electron control layer, and/or the electron transport layer are within these ranges, satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a Li ion, a Na ion, a K ion, a Rb ion, or a Cs ion, and a metal ion of the alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

In an embodiment, the metal-containing material may include a Li complex. The Li complex may include, for example, Compound ET-D1 (Liq) or ET-D2:

ET-D1

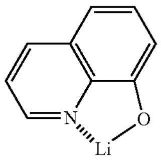

-continued

ET-D2

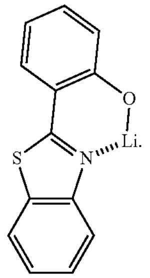

The electron transport region may include an electron injection layer that facilitates injection of electrons from the second electrode 150. The electron injection layer may be in direct contact with the second electrode 150.

The electron injection layer may have i) a single-layered structure consisting of a single layer consisting of a single material, ii) a single-layered structure consisting of a single layer including a plurality of different materials, or iii) a multi-layered structure having a plurality of layers including a plurality of different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may include one or more oxides, halides (for example, fluorides, chlorides, bromides, and/or iodides), and/or tellurides of the alkali metal, the alkaline earth metal, and the rare earth metal, or any combination thereof.

The alkali metal-containing compound may include one or more alkali metal oxides, such as $Li_2O$, $Cs_2O$, and/or $K_2O$, alkali metal halides, such as LiF, NaF, CsF, KF, LiI, NaI, CsI, and/or KI, or any combination thereof. The alkaline earth metal-containing compound may include an alkaline earth metal oxides, such as BaO, SrO, CaO, $Ba_xSr_{1-x}O$ (x is a real number satisfying the condition of $0<x<1$), and/or $Ba_xCa_{1-x}O$ (x is a real number satisfying the condition of $0<x<1$). The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In one or more embodiments, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), as a ligand bonded to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may include (e.g., consist of) an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In an embodiment, the electron injection layer may include (e.g., consist of) i) an alkali metal-containing compound (for example, alkali metal halide), or ii) a) an alkali metal-containing compound (for example, alkali metal halide); and b) an alkali metal, an alkaline earth metal, a rare earth metal, or any combination thereof. In an embodiment, the electron injection layer may be a KI:Yb co-deposited layer, an RbI:Yb co-deposited layer, and/or the like.

When the electron injection layer further includes an organic material, the alkali metal, the alkaline earth metal, the rare earth metal, the alkali metal-containing compound, the alkaline earth metal-containing compound, the rare earth metal-containing compound, the alkali metal complex, the alkaline earth-metal complex, the rare earth metal complex, or any combination thereof may be homogeneously or non-homogeneously dispersed in a matrix including the organic material.

A thickness of the electron injection layer may be in a range of about 1 Å to about 100 Å, and, for example, about 3 Å to about 90 Å. When the thickness of the electron injection layer is within these ranges, satisfactory electron injection characteristics may be obtained without a substantial increase in driving voltage.

Second Electrode 150

The second electrode 150 may be located on the emission layer 130 or the second charge transport layer 140 as described above. In an embodiment, the second electrode 150 may be a cathode, which is an electron injection electrode, and as a material for the second electrode 150, a metal, an alloy, an electrically conductive compound, or any combination thereof, each having a low work function, may be utilized.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including two or more layers.

Capping Layer

A first capping layer may be located outside the first electrode 110 (e.g., located on a side of the first electrode 110 that faces away from the second electrode 150), and/or a second capping layer may be located outside the second electrode 150 (e.g., located on a side of the second electrode 150 that faces away from the first electrode 110).

Light generated in the emission layer 130 may be extracted toward the outside through the first electrode 110, which is a semi-transmissive electrode or a transmissive electrode, and the first capping layer, and/or light generated in the emission layer 130 may be extracted toward the outside through the second electrode 150, which is a semi-transmissive electrode or a transmissive electrode, and the second capping layer.

The first capping layer and the second capping layer may improve the external luminescence efficiency based on the principle of constructive interference. Accordingly, the light extraction efficiency of the light-emitting device 10, 20, 30, and/or 40 may be increased, thereby improving the luminescence efficiency of the light-emitting device 10, 20, 30, and/or 40.

The first capping layer and the second capping layer may each include a material having a refractive index of 1.6 or higher (at 589 nm).

The first capping layer and the second capping layer may each independently be an organic capping layer including an organic material, an inorganic capping layer including an inorganic material, or a composite capping layer including an organic material and an inorganic material.

At least one of the first capping layer and the second capping layer may each independently include one or more carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may be optionally substituted with a substituent including O, N, S, Se, Si, F, Cl, Br, I, or any combination thereof. In an embodiment, at least one of the first capping layer and the second capping layer may each independently include an amine group-containing compound.

In an embodiment, at least one of the first capping layer and the second capping layer may each independently include a compound represented by Formula 201, a compound represented by Formula 202, or any combination thereof.

In one or more embodiments, at least one of the first capping layer and the second capping layer may each independently include one of Compounds HT28 to HT33, one of Compounds CP1 to CP6, β-NPB, or any combination thereof:

CP1

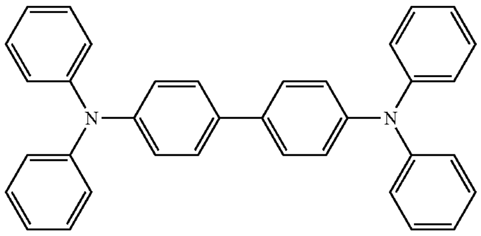

CP2

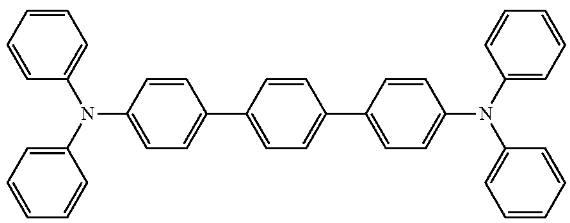

-continued

CP3

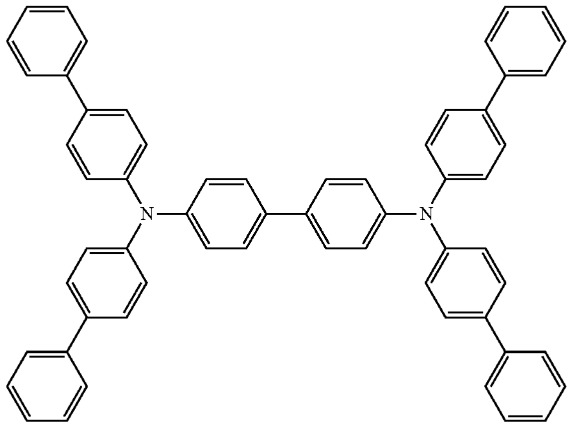

CP4

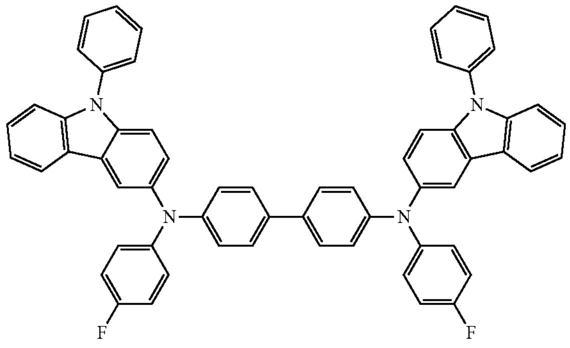

CP5

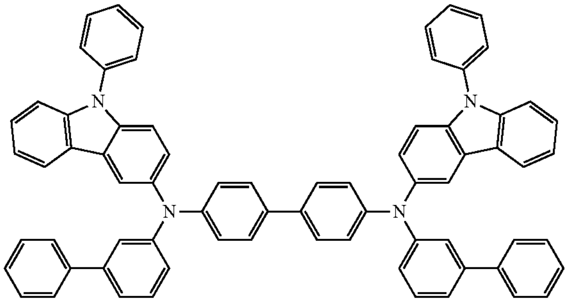

CP6

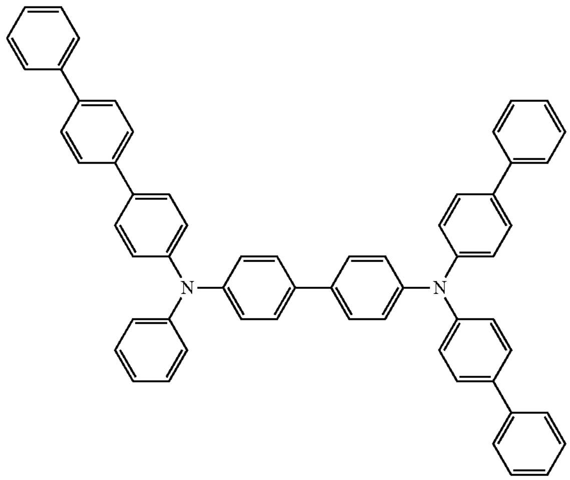

-continued

β-NPB

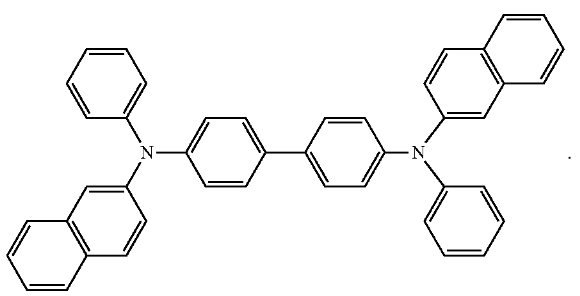

Method of Manufacturing Light-Emitting Device

A method of manufacturing a light-emitting device according to an embodiment may include: preparing a first electrode;

forming a charge transport layer by providing, on the first electrode, an inorganic nanoparticle composition including an inorganic nanoparticle and a solvent, the inorganic nanoparticle including a second ligand bonded to a surface thereof;

forming a preliminary emission layer by providing, on the charge transport layer, a quantum dot composition including a quantum dot, a cross-linking agent, and a solvent, the quantum dot including a first ligand bonded to a surface thereof;

forming an emission layer by performing at least one of a heat treatment and a UV irradiation on the preliminary emission layer; and forming a second electrode on the emission layer.

In an embodiment, the forming of the charge transport layer may include, after providing the inorganic nanoparticle composition on the first electrode, performing a vacuum chamber drying (VCD) process to remove the solvent in a vacuum condition (e.g., atmosphere).

In an embodiment, the inorganic nanoparticle composition may be provided on the first electrode by spin coating and/or ink-jet printing.

In an embodiment, the forming of the emission layer may further include cross-linking the first ligand and the second ligand by performing at least one of a heat treatment and a UV irradiation on the preliminary emission layer. That is, by performing at least one of the heat treatment and the UV irradiation on the preliminary emission layer, a cross-link (e.g., a cross-linked structure) (A) may be formed at an interface between the emission layer and the charge transport layer. The cross-link (A) may include a cross-link in which the first ligand on the surface of the quantum dot and the second ligand on the surface of the inorganic nanoparticle are linked by the cross-linking agent. The cross-linking agent, the quantum dot, and the inorganic nanoparticle are the same as described above.

The heat treatment may be performed at a temperature of about 120° C. to about 200° C., but embodiments are not limited thereto. A cross-link may be formed through the heat treatment, and residual solvent remaining in the preliminary emission layer may be removed.

The UV irradiation may be performed utilizing ultraviolet rays having a wavelength of about 100 nm to about 400 nm, for example, about 250 nm to about 270 nm. A cross-link may be formed through the UV irradiation.

In an embodiment, the forming of the emission layer may further include cross-linking a first ligand on a surface of one quantum dot and a first ligand on a surface of another quantum dot by performing at least one of the heat treatment and the UV irradiation on the preliminary emission layer. That is, by performing at least one of the heat treatment and the UV irradiation on the preliminary emission layer, a cross-link (B) may be further formed in the emission layer.

The forming of the preliminary emission layer may further include, after providing the quantum dot composition on the charge transport layer, performing a VCD process to remove the solvent in a vacuum condition (e.g., atmosphere). After performing the VCD process, an emission layer may be formed through the heat treatment and/or the UV irradiation as described above.

The heat treatment may be performed at a temperature of about 120° C. to about 200° C., but embodiments are not limited thereto. A cross-link may be formed through the heat treatment, and residual solvent remaining in the preliminary emission layer may be removed.

The UV irradiation may be performed utilizing ultraviolet rays having a wavelength of about 100 nm to about 400 nm, for example, about 250 nm to about 270 nm. A cross-link may be formed through the UV irradiation.

By performing the heat treatment and/or UV irradiation on the emission layer, reactions in which the cross-link (A) at the interface between the emission layer and the charge transport layer (e.g., between the quantum dots and the inorganic nanoparticles) and the cross-link (B) in the emission layer (e.g., between the quantum dots) are respectively formed may occur concurrently or simultaneously, but embodiments are not limited thereto.

In an embodiment, the quantum dot composition may be provided on the charge transport layer by spin coating and/or ink-jet printing.

In an embodiment, the method may further include forming a second charge transport layer by providing a second inorganic nanoparticle composition on the emission layer, and the second inorganic nanoparticle composition may include a solvent and an inorganic nanoparticle including a third ligand bonded to a surface thereof.

In an embodiment, the forming of the second charge transport layer may further include cross-linking the first ligand and the third ligand by performing at least one of a heat treatment and a UV irradiation on the second inorganic nanoparticle composition. That is, by performing at least one of the heat treatment and the UV irradiation on the second inorganic nanoparticle composition, a cross-link (e.g., a cross-linked structure) (C) may be formed at an interface between the emission layer and the second charge transport layer. The cross-link (C) may include a cross-link in which the first ligand on the surface of the quantum dot and the third ligand on the surface of the inorganic nanoparticle (e.g., of the second charge transport layer) are linked by the cross-linking agent.

The kind (e.g., type) of the solvent in the inorganic nanoparticle composition and the quantum dot composition is not limited as long as the solvent properly disperses the inorganic nanoparticle and the quantum dot.

In an embodiment, the solvent may be an organic solvent.

In some embodiments, the solvent may include an alcohol-based solvent, a chlorine-based solvent, an ether-based solvent, an ester-based solvent, a ketone-based solvent, an aliphatic hydrocarbon-based solvent, an aromatic hydrocarbon-based solvent, or any combination thereof, but embodiments are not limited thereto.

In some embodiments, the solvent may include methanol, ethanol, propanol, butanol, pentanol, hexanol, heptanol, octanol, nonaol, decanol, dichloromethane, 1,2-dichloroethane, 1,1,2-trichloroethane, chlorobenzene, o-dichlorobenzene, cyclohexylbenzene, tetrahydrofuran, dioxane, anisole, 4-methylanisole, butyl phenyl ether, toluene, xylene, mesitylene, ethylbenzene, n-hexylbenzene, cyclohexylbenzene, trimethylbenzene, tetrahydronaphthalene, cyclohexane, methylcyclohexane, n-pentane, n-hexane, n-heptane, n-octane, n-nonane, n-decane, dodecane, hexadecane, octadecane, acetone, methylethylketone, cyclohexanone, acetophenone, ethyl acetate, butyl acetate, methyl cellosolve acetate, ethyl cellosolve acetate, methyl benzoate, ethyl benzoate, butyl benzoate, 3-phenoxy benzoate, or any combination thereof, but embodiments are not limited thereto.

The amount of the solvent may be from 80 wt % or more to 99.9 wt % or less, for example, from 90 wt % or more to 99.8 wt % or less, based on the total weight of the quantum dot composition, but embodiments are not limited thereto. Within these ranges, the quantum dot composition may have a solid concentration suitable for a solution process.

The quantum dot composition may have a viscosity of about 1 cP to about 10 cP. The quantum dot composition may have a surface tension of about 10 dynes/cm to about 40 dynes/cm, for example, about 20 dynes/cm to about 40 dynes/cm. When the viscosity and/or the surface tension are within these ranges, the quantum dot composition may be suitable for manufacturing a quantum dot emission layer of a light-emitting device by utilizing a solution process.

The quantum dot composition may have a vapor pressure of about $10^{-5}$ mmHg to about $10^{-2}$ mmHg at 25° C., but embodiments are not limited thereto. Within this range, the quantum dot composition may be suitable for manufacturing a quantum dot emission layer of a light-emitting device by utilizing a solution process, for example, an ink-jet printing.

In an embodiment, the amount of the cross-linking agent may be from about 0.01 wt % to about 1 wt %, based on the total weight of the quantum dot composition, but embodiments are not limited thereto.

The quantum dot composition may further include an additive for purposes such as photo-curing, energy band level control, charge mobility control, and/or coating uniformity improvement.

The additive may include a photoinitiator, a dispersant, an adhesion promoter, a leveling agent, an antioxidant, an ultraviolet absorber, or any combination thereof. In an embodiment, the quantum dot composition may further include a photoinitiator.

In an embodiment, the quantum dot composition may further include a dispersant to improve the degree of dispersion of quantum dots.

The dispersant may be utilized to prevent or substantially prevent aggregation of quantum dots in the quantum dot composition and to act as a protective layer for the quantum dots during a solution process.

The dispersant may include anionic, cationic, and/or nonionic polymeric materials.

The amount of the dispersant may be from about 10 parts by weight to about 50 parts by weight, for example, about 15 parts by weight to about 30 parts by weight, based on 100 parts by weight of the quantum dots. When the amount of the dispersant is within these ranges, the aggregation of the quantum dots in the quantum dot composition may be substantially prevented or reduced, and the dispersant may act as a protective layer for the quantum dots.

The adhesion promoter may be added to increase adhesion to a substrate, and may include a silane coupling agent having a reactive substituent selected from a carboxyl group, a methacryloyl group, an isocyanate group, an epoxy group, and a combination thereof, but embodiments are not limited thereto. In an embodiment, the silane coupling agent may include trimethoxysilylbenzoic acid, γ-methacryloxypropyltrimethoxysilane, vinyltriacetoxysilane, vinyltrimethoxysilane, γ-isocyanatepropyltriethoxysilane, γ-glycidoxypropyltrimethoxysilane, β-(3,4-epoxycyclohexyl)ethyltrimethoxysilane, or any combination thereof.

The leveling agent may be added to improve coatability of the quantum dot composition. The leveling agent may include, for example, a silicon-based compound, a fluorine-based compound, a siloxane-based compound, a nonionic surfactant, an ionic surfactant, a titanate coupling agent, and/or the like, but embodiments are not limited thereto.

The silicon-based compound may include, but not particularly limited to, dimethyl silicon, methyl silicon, phenyl silicon, methyl phenyl silicon, alkyl-modified silicon, alkoxy-modified silicon, polyether-modified silicon, and/or the like.

The fluorine-based compound may include, but not particularly limited to, polytetrafluoroethylene, polyvinylidene fluoride, fluoroalkyl methacrylate, perfluoropolyether, perfluoroalkyl ethylene oxide, and/or the like.

The siloxane-based compound may include, but not particularly limited to, dimethyl siloxane compounds (product names: KF96L-1, KF96L-5, KF96L-10, and KF96L-100, products of Shin-Etsu Silicone Co., Ltd.).

The amount of the leveling agent may vary depending on the desired function, but may be from about 0.001 wt % to about 5 wt %, for example, from about 0.001 wt % to about 1 wt %, based on the total weight of the quantum dot composition. When the amount of the leveling agent is within these ranges, fluidity and film uniformity of the quantum dot composition may be improved.

The quantum dot composition has suitable or excellent ink-jet discharge stability, and thus may be, for example, a quantum dot composition for ink-jet printing, but embodiments are not limited thereto.

Respective layers included in the hole transport region and respective layers included in the electron transport region may be formed in a certain region by utilizing one or more suitable methods selected from vacuum deposition, spin coating, casting, Langmuir-Blodgett (LB) deposition, ink-jet printing, laser-printing, and laser-induced thermal imaging. When respective layers included in the hole transport region and respective layers included in the electron transport region are formed by vacuum deposition, the vacuum deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of the layer to be formed.

Electronic Apparatus

The light-emitting device 10, 20, 30, and/or 40 may be included in various suitable electronic apparatuses. In an embodiment, an electronic apparatus including the light-emitting device 10, 20, 30, and/or 40 may be a light-emitting apparatus or an authentication apparatus.

The electronic apparatus (for example, a light-emitting apparatus) may further include, in addition to the light-emitting device 10, 20, 30, and/or 40, i) a color filter, ii) a color conversion layer, or iii) a color filter and a color conversion layer. The color filter and/or the color conversion layer may be disposed on at least one traveling direction of light emitted from the light-emitting device 10, 20, 30, and/or 40. In an embodiment, the light emitted from the light-emitting device 10, 20, 30, and/or 40 may be blue light or white light. The light-emitting device 10, 20, 30, and/or 40 is the same as described above. In an embodiment, the color conversion layer may include quantum dots. The quantum dots may be, for example, the quantum dots described herein.

The electronic apparatus may include a first substrate. The first substrate may include a plurality of sub-pixel areas, the color filter may include a plurality of color filter areas respectively corresponding to the plurality of sub-pixel areas, and the color conversion layer may include a plurality of color conversion areas respectively corresponding to the plurality of sub-pixel areas.

A pixel-defining film may be located between the plurality of sub-pixel areas to define each sub-pixel area.

The color filter may further include a plurality of color filter areas and light-shielding patterns between the plurality of color filter areas, and the color conversion layer may further include a plurality of color conversion areas and light-shielding patterns between the plurality of color conversion areas.

The plurality of color filter areas (or a plurality of color-conversion areas) may include: a first area to emit a first color light; a second area to emit a second color light; and/or a third area to emit a third color light, and the first color light, the second color light, and/or the third color light may have different maximum emission wavelengths. In an embodiment, the first color light may be red light, the second color light may be green light, and the third color light may be blue light. In an embodiment, the plurality of color filter areas (or the plurality of color conversion areas) may include quantum dots. In some embodiments, the first area may include a red quantum dot, the second area may include a green quantum dot, and the third area may not include a quantum dot. The quantum dot is the same as described in the present specification. The first area, the second area, and/or the third area may each further include a scatterer.

In an embodiment, the light-emitting device 10, 20, 30, and/or 40 may emit a first light, the first area may absorb the first light to emit a first first-color light, the second area may absorb the first light to emit a second first-color light, and the third area may absorb the first light to emit a third first-color light. In this regard, the first first-color light, the second first-color light, and the third first-color light may have different maximum emission wavelengths. In an embodiment, the first light may be blue light, the first first-color light may be red light, the second first-color light may be green light, and the third first-color light may be blue light.

The electronic apparatus may further include a thin-film transistor, in addition to the light-emitting device 10, 20, 30, and/or 40. The thin-film transistor may include a source electrode, a drain electrode, and an activation layer, wherein one of the source electrode and the drain electrode may be electrically connected to one of the first electrode and the second electrode of the light-emitting device 10, 20, 30, and/or 40.

The thin-film transistor may further include a gate electrode, a gate insulating film, and/or the like.

The activation layer may include crystalline silicon, amorphous silicon, organic semiconductor, oxide semiconductor, and/or the like.

The light-emitting apparatus may further include a sealing portion for sealing the light-emitting device 10, 20, 30, and/or 40. The sealing portion may be located between the color filter and/or the color conversion layer and the light-emitting device 10, 20, 30, and/or 40. The sealing portion allows light from the light-emitting device 10, 20, 30, and/or 40 to be extracted to the outside, while concurrently or simultaneously preventing or substantially preventing ambient air and/or moisture from penetrating into the light-emitting device 10, 20, 30, and/or 40. The sealing portion may be a sealing substrate including a transparent glass substrate or a plastic substrate. The sealing portion may be a thin-film encapsulation layer including an organic layer and/or an inorganic layer. When the sealing portion is a thin-film encapsulation layer, the electronic apparatus may be flexible.

Various suitable functional layers may be additionally located on the sealing portion, in addition to the color filter and/or the color conversion layer, according to the usage of the electronic apparatus. Examples of the functional layer may include a touch screen layer, a polarization layer, or the like. The touch screen layer may be a pressure-sensitive touch screen layer, a capacitive touch screen layer, or an infrared touch screen layer. The authentication apparatus may be, for example, a biometric authentication apparatus that identifies an individual according to biometric information (e.g., a fingertip, a pupil, and/or the like).

The authentication apparatus may further include a biometric information collector, in addition to the light-emitting device 10, 20, 30, and/or 40.

The electronic apparatus may be applied to various suitable displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, and/or endoscope displays), fish finders, various measuring instruments, meters (for example, meters for a vehicle, an aircraft, and/or a vessel), projectors, and/or the like.

Figure 5:
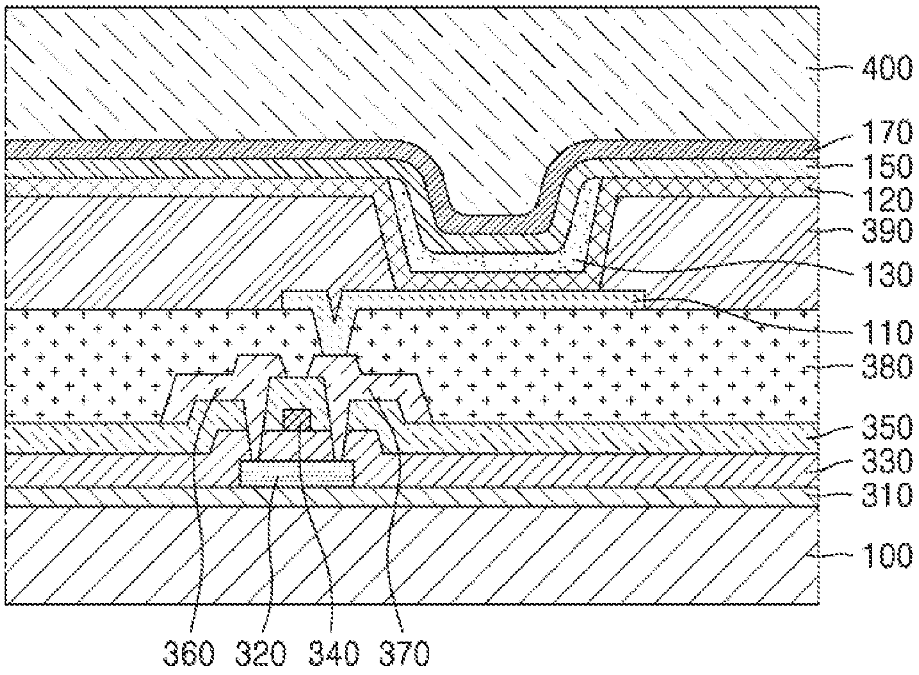
FIG. 5 is a schematic cross-sectional view of a light-emitting apparatus according to an embodiment.
Figure 6:
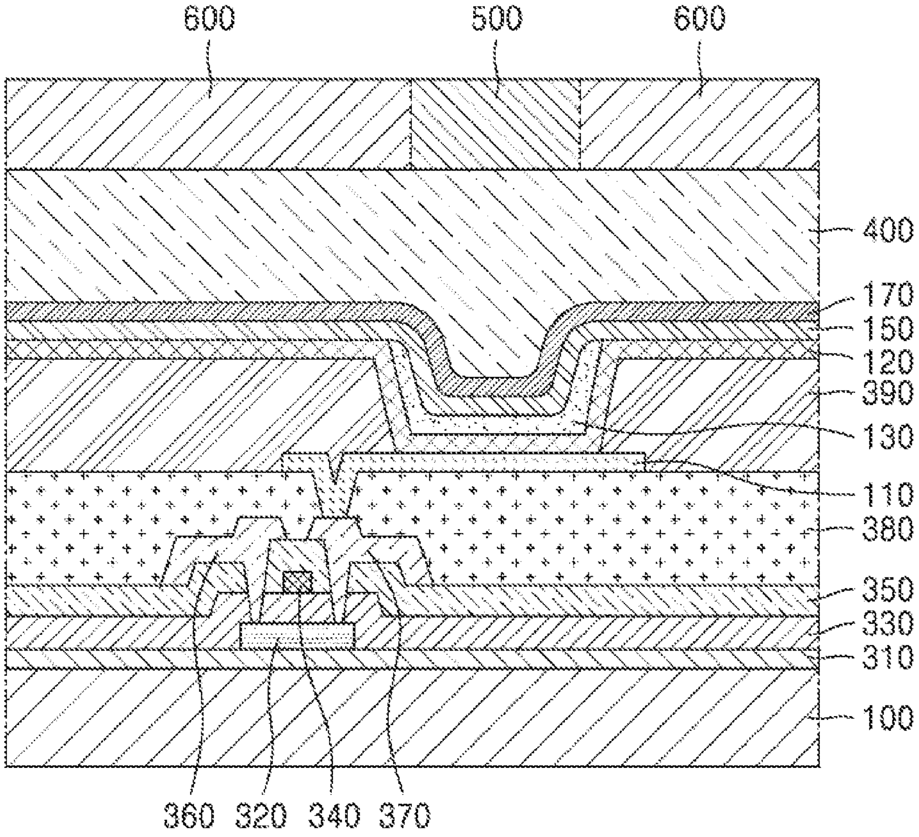
FIG. 6 is a schematic cross-sectional view of a light-emitting apparatus according to another embodiment.

Description of FIGS. 5 and 6

FIG. 5 is a cross-sectional view of a light-emitting apparatus according to an embodiment.

The light-emitting apparatus of FIG. 5 includes a substrate 100, a thin-film transistor (TFT), a light-emitting device, and an encapsulation portion 400 that seals the light-emitting device.

The substrate 100 may be a flexible substrate, a glass substrate, or a metal substrate. A buffer layer 310 may be located on the substrate 100. The buffer layer 310 may prevent or substantially prevent penetration of impurities through the substrate 100 and provide a flat surface on the substrate 100.

A TFT may be located on the buffer layer 310. The TFT may include an activation layer 320, a gate electrode 340, a source electrode 360, and a drain electrode 370.

The activation layer 320 may include an inorganic semiconductor such as silicon and/or polysilicon, an organic semiconductor, and/or an oxide semiconductor, and may include a source region, a drain region, and a channel region.

A gate insulating film 330 for insulating the activation layer 320 from the gate electrode 340 may be located on the activation layer 320, and the gate electrode 340 may be located on the gate insulating film 330.

An interlayer insulating film 350 may be located on the gate electrode 340. The interlayer insulating film 350 may be located between the gate electrode 340 and the source electrode 360 to insulate the gate electrode 340 from the source electrode 360 and between the gate electrode 340 and the drain electrode 370 to insulate the gate electrode 340 from the drain electrode 370.

The source electrode 360 and the drain electrode 370 may be located on the interlayer insulating film 350. The interlayer insulating film 350 and the gate insulating film 330 may be formed to expose the source region and the drain region of the activation layer 320, and the source electrode 360 and the drain electrode 370 may be in contact with the exposed portions of the source region and the drain region of the activation layer 320.

The TFT is electrically connected to a light-emitting device to drive the light-emitting device, and is covered by a passivation layer 380. The passivation layer 380 may include an inorganic insulating film, an organic insulating film, or a combination thereof. A light-emitting device is provided on the passivation layer 380. The light-emitting device includes a first electrode 110, an emission layer 130, and a second electrode 150.

The first electrode 110 may be located on the passivation layer 380. The passivation layer 380 may not completely cover the drain electrode 370 and expose a portion of the drain electrode 370, and the first electrode 110 may be disposed to connect to the exposed portion of the drain electrode 370.

A pixel-defining film 390 including an insulating material may be located on the first electrode 110. The pixel-defining film 390 may expose a region of the first electrode 110, and an emission layer 130 may be formed in the exposed region of the first electrode 110. The pixel-defining film 390 may be a polyimide or polyacryl organic film. In some embodiments, at least some layers of the emission layer 130 may extend beyond the upper portion of the pixel-defining film 390 to be located in the form of a common layer.

The second electrode 150 may located be on the emission layer 130, and a capping layer 170 may be additionally formed on the second electrode 150. The capping layer 170 may be formed to cover the second electrode 150.

The encapsulation portion 400 may be located on the capping layer 170. The encapsulation portion 400 may be located on a light-emitting device to protect the light-emitting device from moisture and/or oxygen. The encapsulation portion 400 may include: an inorganic film including silicon nitride ($SiN_x$), silicon oxide ($SiO_x$), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, and/or the like), an epoxy-based resin (for example, aliphatic glycidyl ether (AGE), and/or the like), or a combination thereof; or a combination of the inorganic film and the organic film.

FIG. 6 is a cross-sectional view of a light-emitting apparatus according to another embodiment.

The light-emitting apparatus of FIG. 6 is the same as the light-emitting apparatus of FIG. 5, except that a light-shielding pattern 600 and a functional region 500 are additionally located on the encapsulation portion 400. The functional region 500 may be i) a color filter area, ii) a color conversion area, or iii) a combination of the color filter area and the color conversion area. In an embodiment, the light-emitting device included in the light-emitting apparatus of FIG. 6 may be a tandem light-emitting device.

Definition of Terms

The term "$C_3$-$C_{60}$ carbocyclic group" as used herein refers to a cyclic group consisting of only carbon atoms as a ring-forming atom and having 3 to 60 carbon atoms, and the term "$C_1$-$C_{60}$ heterocyclic group" as used herein refers to a cyclic group that has 1 to 60 carbon atoms and further has, in addition to carbon atoms, a heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are condensed (e.g., combined together) with each other. In an embodiment, the $C_1$-$C_{60}$ heterocyclic group may have 3 to 61 ring-forming atoms.

The term "cyclic group" as used herein may include the $C_3$-$C_{60}$ carbocyclic group and the $C_1$-$C_{60}$ heterocyclic group.

The term "π electron-rich $C_3$-$C_{60}$ cyclic group" as used herein refers to a cyclic group that has 3 to 60 carbon atoms and does not include *—N=*' as a ring-forming moiety, and the term "π electron-deficient nitrogen-containing $C_1$-$C_{60}$ cyclic group" as used herein refers to a heterocyclic group that has 1 to 60 carbon atoms and includes *—N=*' as a ring-forming moiety.

In an embodiment, the $C_3$-$C_{60}$ carbocyclic group may be i) a T1 group or ii) a condensed cyclic group in which at least two T1 groups are condensed (e.g., combined together) with each other (for example, the $C_3$-$C_{60}$ carbocyclic group may be a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be i) a T2 group, ii) a condensed cyclic group in which at least two T2 groups are condensed (e.g., combined together) with each other, or iii) a condensed cyclic group in which at least one T2 group and at least one T1 group are condensed (e.g., combined together) with each other (for example, the $C_1$-$C_{60}$ heterocyclic group may be a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be i) a T1 group, ii) a condensed cyclic group in which at least two T1 groups are condensed (e.g., combined together) with each other, iii) a T3 group, iv) a condensed cyclic group in which at least two T3 groups are condensed (e.g., combined together) with each other, or v) a condensed cyclic group in which at least one T3 group and at least one T1 group are condensed (e.g., combined together) with each other (for example, the π electron-rich $C_3$-$C_{60}$ cyclic group may be the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be i) a T4 group, ii) a condensed cyclic group in which at least two T4 groups are condensed (e.g., combined together) with each other, iii) a condensed cyclic group in which at least one T4 group and at least one T1 group are condensed (e.g., combined together) with each other, iv) a condensed cyclic group in which at least one T4 group and at least one T3 group are condensed (e.g., combined together) with each other, or v) a condensed cyclic group in which at least one T4 group, at least one T1 group, and at least one T3 group are condensed (e.g., combined together) with one another (for example, the π electron-deficient nitrogen-containing $C_1$-$C_{60}$ cyclic group may be a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), wherein the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group," "the $C_3$-$C_{60}$ carbocyclic group," "the $C_1$-$C_{60}$ heterocyclic group," "the π electron-rich $C_3$-$C_{60}$ cyclic group," or "the π electron-deficient nitrogen-containing $C_1$-$C_{60}$ cyclic group" as used herein refer to a group condensed (e.g., combined together) with any suitable cyclic group, a monovalent group, or a polyvalent group (for example, a divalent group, a trivalent group, a tetravalent group, etc.), depending on the structure of a formula in connection with which the terms are utilized. In an embodiment, "a benzene group" may be a benzo group, a phenyl group, a phenylene group, or the like, which may be easily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$- $C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group. Examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group.

The term "$C_1$-$C_{60}$ alkyl group" as used herein refers to a linear or branched aliphatic hydrocarbon saturated monovalent group that has 1 to 60 carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a secnonyl group, a tert-nonyl group, an n-decyl group, an isodecyl group, a sec-decyl group, and a tert-decyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a monovalent hydrocarbon group having at least one carbon-carbon double bond at a main chain (e.g., in the middle) or at a terminal end (e.g., the terminus) of the $C_2$-$C_{60}$ alkyl group, and examples thereof may include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a monovalent hydrocarbon group having at least one carbon-carbon triple bond at a main chain (e.g., in the middle) or at a terminal end (e.g., the terminus) of the $C_2$-$C_{60}$ alkyl group, and examples thereof may include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof may include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and examples thereof may include a cyclopropyl group, a cyclobutyl group, a cyclopentyl group, a cyclohexyl group, a cycloheptyl group, a cyclooctyl group, an adamantyl group, a norbornyl group (or a bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent cyclic group that further includes, in addition to 1 to 10 carbon atoms, at least one heteroatom as a ring-forming atom, and examples thereof may include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent cyclic group that has 3 to 10 carbon atoms and at least one carbon-carbon double bond in the ring thereof and no aromaticity, and examples thereof may include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent cyclic group that has, in addition to 1 to 10 carbon atoms, at least one heteroatom as a ring-forming atom, and at least one double bond in the cyclic structure thereof. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, a fluorenyl group, and an ovalenyl group. When the $C_6$-$C_{60}$ aryl group and the $C_6$-$C_{60}$ arylene group each independently include two or more rings, the rings may be condensed (e.g., combined together) with each other.

The term "$C_1$-$C_{60}$ heteroaryl group" as used herein refers to a monovalent group having a heterocyclic aromatic system that has, in addition to 1 to 60 carbon atoms, at least one heteroatom as a ring-forming atom. The term "$C_1$-$C_{60}$ heteroarylene group" as used herein refers to a divalent group having a heterocyclic aromatic system that has, in addition to 1 to 60 carbon atoms, at least one heteroatom as a ring-forming atom. Examples of the $C_1$-$C_{60}$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, a carbazolyl group, a dibenzofuranyl group, a dibenzothiofuranyl group, and a naphthyridinyl group. When the $C_1$-$C_{60}$ heteroaryl group and the $C_1$-$C_{60}$ heteroarylene group each include two or more rings, the rings may be condensed (e.g., combined together) with each other.

The term "monovalent non-aromatic condensed polycyclic group" as used herein refers to a monovalent group having two or more rings condensed (e.g., combined together) and only carbon atoms (for example, 8 to 60 carbon atoms) as ring-forming atoms, wherein the molecular structure as a whole is non-aromatic. Examples of the monovalent non-aromatic condensed polycyclic group may include an indenyl group, a fluorenyl group, a spiro-bifluorenyl group, a benzofluorenyl group, an indenophenanthrenyl group, an adamantyl group, and an indeno anthracenyl group. The term "divalent non-aromatic condensed polycyclic group" as used herein refers to a divalent group having the same structure as a monovalent non-aromatic condensed polycyclic group.

The term "monovalent non-aromatic condensed heteropolycyclic group" as used herein refers to a monovalent group having two or more rings condensed (e.g., combined together), and at least one heteroatom other than carbon atoms (for example, having 1 to 60 carbon atoms) as ring-forming atoms, wherein the molecular structure as a whole is non-aromatic. Examples of the monovalent non-aromatic condensed heteropolycyclic group may include a 9,9-dihydroacridinyl group, an azaadamantyl group, and a 9H-xanthenyl group. The term "divalent non-aromatic condensed heteropolycyclic group" as used herein refers to a divalent group having the same structure as a monovalent non-aromatic condensed heteropolycyclic group.

The term "$C_6$-$C_{60}$ aryloxy group" as used herein is represented by —$OA_{102}$ (wherein $A_{102}$ is the $C_6$-$C_{60}$ aryl group), and the term "$C_6$-$C_{60}$ arylthio group" as used herein is represented by —$SA_{103}$ (wherein $A_{103}$ is the $C_6$-$C_{60}$ aryl group).

The term "$C_7$-$C_{60}$ aryl alkyl group" as used herein is represented by -$A_{104}A_{105}$ (where $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group" as used herein is represented by -$A_{106}A_{107}$ (where $A_{106}$ may be a $C_1$-$C_{59}$ alkylene group, and $A_{107}$ may be a $C_1$-$C_{59}$ heteroaryl group).

The term "$R_{10a}$" as used herein refers to:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

$Q_1$ to $Q_3$, $Q_{11}$ to $Q_{13}$, $Q_{21}$ to $Q_{23}$, and $Q_{31}$ to $Q_{33}$ as used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein refers to any atom other than a carbon atom. Examples of the heteroatom may include O, S, N, P, Si, B, Ge, Se, or any combination thereof.

The term "Ph" as used herein refers to a phenyl group, the term "Me" as used herein refers to a methyl group, the term "Et" as used herein refers to an ethyl group, the term "tert-Bu," "$^t$Bu," or "Bu$^t$" as used herein refers to a tert-butyl group, and the term "OMe" as used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula or moiety.

Hereinafter, a light-emitting device according to an embodiment will be described in more detail with reference to Examples.

EXAMPLE

Preparation Example 1: Preparation of Quantum Dot Composition 0.2 mmol of indium acetate, 0.6 mmol of oleic acid, and 10 ml of 1-octadecene were mixed in a three-necked flask, and then, oxygen and moisture were removed therefrom while degassing and stirring at 120° C. for 60 minutes under vacuum to form a reaction solution. Subsequently, the reaction solution was heated up to 280° C. in a nitrogen atmosphere, and then, a mixed solution including 0.1 mmol of tris(trimethylsilyl)phosphine and 0.5 ml of trioctylphosphine was added thereto, and the reaction solution was reacted for 20 minutes. Acetone was added to the reaction solution which had been cooled to room temperature, and then, a precipitate obtained by centrifugation was re-dispersed in toluene to synthesize an InP quantum dot core.

In forming a quantum dot shell, 0.3 mmol of zinc acetate, 0.6 mmol of oleic acid, and 10 ml of a trioctylamine solution were added to a three-necked flask, and then, oxygen and moisture were removed therefrom while degassing and stirring at 120° C. for 60 minutes to form a reaction solution. Subsequently, the reaction solution was heated up to 220° C. in a nitrogen atmosphere, and then, the InP quantum dot core and 0.6 mmol of a solution in which sulfur was dissolved in trioctylphosphine were added thereto, and the reaction solution was heated up to 280° C. and reacted for 30 minutes. After completion of the reaction, acetone was added to the solution, which had been cooled to room temperature, and then, centrifugation was performed thereon to obtain an InP quantum dot core/ZnS shell material (e.g., InP/ZnS quantum dot).

The quantum dot composition of Example 1 was prepared by mixing the synthesized InP/ZnS quantum dot, cyclohexylbenzene, and a 4,4'-diazido-octafluoro-1,1'-biphenyl cross-linking agent, and the amount of the quantum dot was 3 wt %, and the amount of the 4,4'-diazido-octafluoro-1,1'-biphenyl cross-linking agent was 0.5 wt %, based on the total weight of the quantum dot composition. The quantum dot composition of Comparative Example 1 has the same composition as the quantum dot composition of Example 1 except for the cross-linking agent (e.g., not having the cross-linking agent).

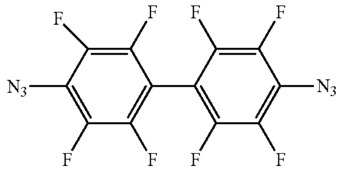

<4,4′-diazido-octafluoro-1,1′-biphenyl>

Example 1

In manufacturing a light-emitting device, on an ITO (anode) substrate with patterns formed thereon, a hole transport layer, a quantum dot emission layer, an electron transport layer, and a cathode were sequentially manufactured. A charge transport layer and the quantum dot emission layer were formed by spin coating, and the cathode was manufactured by deposition. The hole transport layer was formed to a thickness of 30 nm utilizing NiO nanoparticles having oleic acid surface ligands. The quantum dot emission layer having 1-dodecanethiol surface ligands was formed to a thickness of 20 nm. The electron transport layer was formed to a thickness of 40 nm utilizing ZnO having propyltrimethoxysilane surface ligands. In forming the quantum dot emission layer, after performing spin coating, a VCD process was performed until pressure reached $10^{-3}$ mmHg, and after performing the VCD process, the product was exposed to a wavelength of 254 nm for 10 seconds. Subsequently, a baking process was performed at 150° C. for 30 minutes. In forming the charge transport layer, after performing spin coating, a VCD process was performed until pressure reached $10^{-3}$ mmHg, and after performing the VCD process, a baking process was performed at 150° C. for 30 minutes.

Comparative Example 1

In manufacturing a light-emitting device, on an ITO (anode) substrate with patterns formed thereon, a hole transport layer, a quantum dot emission layer, an electron transport layer, and a cathode were sequentially manufactured (e.g., formed). A charge transport layer and the quantum dot emission layer were formed by spin coating, and the cathode was manufactured by deposition. The hole transport layer was formed to a thickness of 30 nm utilizing NiO nanoparticles having oleic acid surface ligands. The quantum dot emission layer having 1-dodecanethiol surface ligands was formed to a thickness of 20 nm. The electron transport layer was formed to a thickness of 40 nm utilizing ZnO having propyltrimethoxysilane surface ligands. In forming the quantum dot emission layer and each charge transport layer, after performing spin coating, a VCD process was performed until pressure reached $10^{-3}$ mmHg, and after performing the VCD process, a baking process was performed at 150° C. for 30 minutes.

Figure 7:
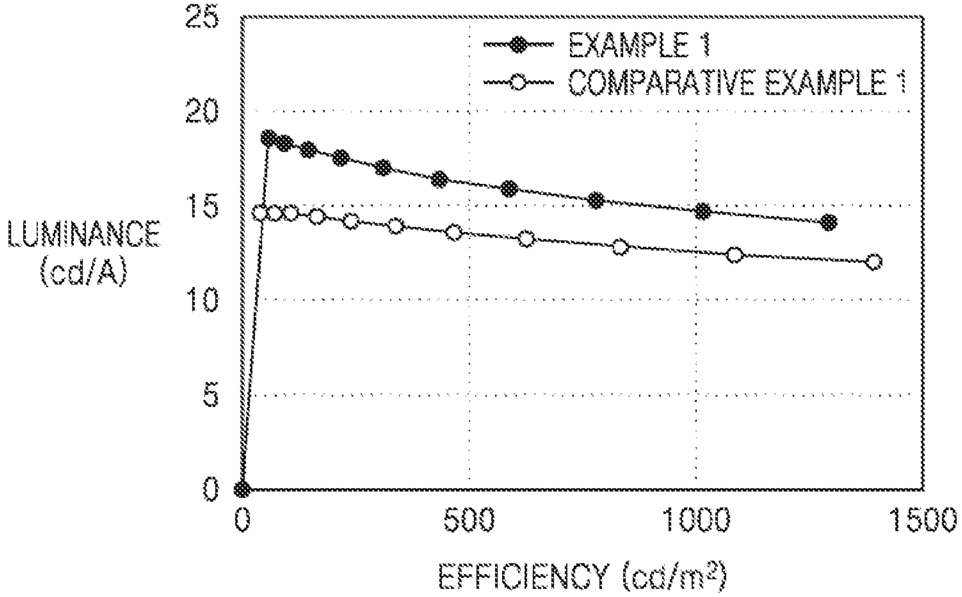
FIG. 7 is a graph showing luminance characteristics versus efficiency of light-emitting devices manufactured according to Example 1 and Comparative Example 1.

FIG. 7 is a graph showing efficiency-luminance characteristics of the light-emitting devices manufactured according to Example 1 and Comparative Example 1. Referring to FIG. 7, it is confirmed that the light-emitting device of Example 1 has improved efficiency compared to the light-emitting device of Comparative Example 1.

A light-emitting device according to the present disclosure may have improved efficiency and lifespan due to an increased interlayer bonding force between an emission layer and a charge transport layer, and may be implemented in a flexible device.

As used herein, the terms "substantially," "about," and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, or 5% of the stated value.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims, and equivalents thereof.

What is claimed is:

1. A light-emitting device comprising:

a first electrode;

a second electrode facing the first electrode;

an emission layer between the first electrode and the second electrode and comprising a quantum dot comprising a first ligand bonded to a surface thereof; and a charge transport layer between the first electrode and the emission layer and comprising an inorganic nanoparticle and a second ligand coordinate-bonded to a surface of the inorganic nanoparticle, wherein an interface between the emission layer and the charge transport layer comprises a cross-link in which the first ligand on the surface of the quantum dot and the second ligand on the surface of the inorganic nanoparticle are linked by a cross-linking agent.

2. The light-emitting device of claim 1, wherein the cross-linking agent comprises two or more functional groups, and the two or more functional groups are each independently an azide group, an alkoxy group, a vinyl group, a thiol group, an amine group, an epoxy group, an oxirane group, a carboxyl group, or any combination thereof.

3. The light-emitting device of claim 1, wherein the cross-linking agent comprises two or more functional groups, and the two or more functional groups are each an azide group.

4. The light-emitting device of claim 1, wherein the cross-linking agent is at least one selected from following compounds:

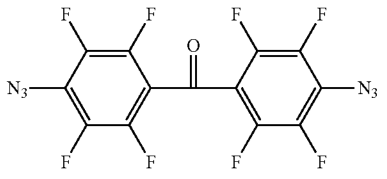

-continued

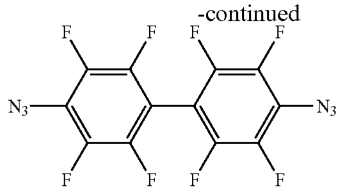

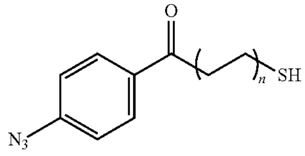

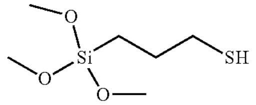

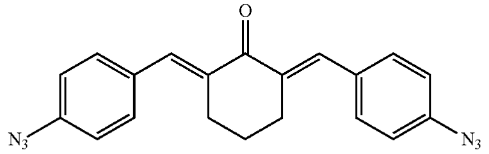

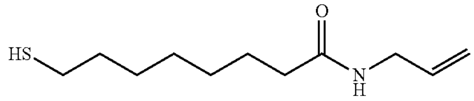

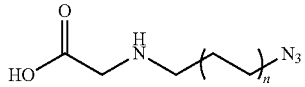

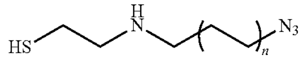

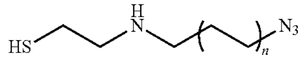

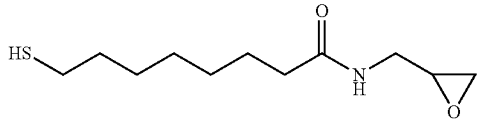

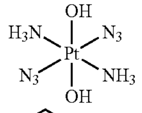

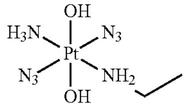

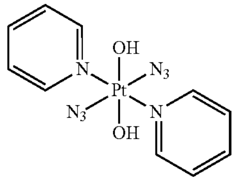

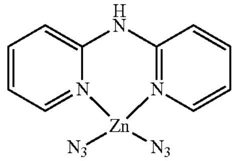, wherein, n is an integer from 1 to 5.

5. The light-emitting device of claim 1, wherein the first ligand bonded to the surface of the quantum dot is oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, or any combination thereof.

6. The light-emitting device of claim 1, wherein the first electrode is an anode, the second electrode is a cathode, and the charge transport layer is a hole transport layer.

7. The light-emitting device of claim 6, wherein the inorganic nanoparticle in the hole transport layer comprises $WO_2$, $WO_3$, NiO, $MoO_3$, $Cr_2O_3$, $Bi_2O_3$, CuO, $Cu_2O$, CuI, CuSCN, $Nb_2O_5$, $BaSnO_3$, $Zn_2SnO_4$, $SrTiO_3$, $Zn_2TiO_8$, or any combination thereof.

8. The light-emitting device of claim 6, wherein the second ligand bonded to the surface of the inorganic nanoparticle in the hole transport layer is oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, alkyl trimethoxy silane, mercaptopropionic acid, tert-butoxyamino acid, carbazole-substituted alkyl carboxylic acid, pyrene-substituted alkyl carboxylic acid, or any combination thereof.

9. The light-emitting device of claim 1, wherein the first electrode is a cathode, the second electrode is an anode, and the charge transport layer is an electron transport layer.

10. The light-emitting device of claim 9, wherein the inorganic nanoparticle in the electron transport layer comprises ZnO, $TiO_2$, $SnO_2$, $In_2O_3$, $WO_3$, $Nb_2O_3$, $CeO_x$, Al-doped ZnO, Mg-doped ZnO, Li-doped ZnO, Y-doped ZnO, Al-doped $TiO_2$, Mg-doped $TiO_2$, Li-doped $TiO_2$, Y-doped $TiO_2$, or any combination thereof.

11. The light-emitting device of claim 9, wherein the second ligand bonded to the surface of the inorganic nanoparticle in the electron transport layer is oleic acid, oleyl amine, 1-dodecanethiol, trioctylphosphine oxide, 2-ethylhexane-1-thiol, caproic acid, propionic acid, benzoic acid, cinnamic acid, thiophenol, adamantyl acid, alkyl trimethoxy silane, mercaptopropionic acid, tert-butoxyamino acid, carbazole-substituted alkyl carboxylic acid, pyrene-substituted alkyl carboxylic acid, or any combination thereof.

12. The light-emitting device of claim 1, wherein the quantum dot comprises a first quantum dot and a second quantum dot, and the emission layer comprises a cross-link in which a first ligand on a surface of the first quantum dot and a first ligand on a surface of the second quantum dot are linked by the cross-linking agent.

13. The light-emitting device of claim 1, further comprising a second charge transport layer between the emission layer and the second electrode and comprising an inorganic nanoparticle comprising a third ligand bonded to a surface thereof, wherein an interface between the emission layer and the second charge transport layer comprises a cross-link in which the first ligand on the surface of the quantum dot and the third ligand on the surface of the inorganic nanoparticle in the second charge transport layer are linked by the cross-linking agent.

14. The light-emitting device of claim 1, wherein the emission layer comprises a first emission layer and a second emission layer, the first emission layer being between the first electrode and the second emission layer, the quantum dot comprises a first quantum dot and a second quantum dot, a first ligand bonded to a surface of the first quantum dot in the first emission layer is a hole-transporting ligand, and a first ligand bonded to a surface of the second quantum dot in the second emission layer is an electron-transporting ligand.

15. A method of manufacturing a light-emitting device, the method comprising:

preparing a first electrode;

forming a charge transport layer by providing, on the first electrode, an inorganic nanoparticle composition comprising an inorganic nanoparticle and a solvent, the inorganic nanoparticle comprising a second ligand bonded to a surface thereof;

forming a preliminary emission layer by providing, on the charge transport layer, a quantum dot composition comprising a quantum dot, a cross-linking agent, and a solvent, the quantum dot comprising a first ligand bonded to a surface thereof;

forming an emission layer by performing at least one selected from among a heat treatment and a UV irradiation on the preliminary emission layer; and forming a second electrode on the emission layer.

16. The method of claim 15, wherein the forming of the emission layer further comprises cross-linking the first ligand and the second ligand by performing the at least one selected from among the heat treatment and the UV irradiation on the preliminary emission layer.

17. The method of claim 15, wherein the forming of the emission layer further comprises cross-linking a first ligand on a surface of a first quantum dot included in the quantum dot and a first ligand on a surface of a second quantum dot included in the quantum dot by performing the at least one selected from among the heat treatment and the UV irradiation on the preliminary emission layer.

18. The method of claim 15, further comprising forming a second charge transport layer by providing a second inorganic nanoparticle composition on the emission layer, wherein the second inorganic nanoparticle composition comprises a solvent and an inorganic nanoparticle comprising a third ligand bonded to a surface thereof.

19. The method of claim 18, wherein the forming of the second charge transport layer further comprises cross-linking the first ligand and the third ligand by performing at least one selected from among a heat treatment and a UV irradiation on the second inorganic nanoparticle composition.

20. The method of claim 15, wherein the quantum dot composition has a viscosity of about 1 cP to about 10 cP and a surface tension of about 10 dynes/cm to about 40 dynes/cm.

* * * * *